(12) United States Patent
Olsen et al.

(10) Patent No.: US 8,083,751 B2
(45) Date of Patent: Dec. 27, 2011

(54) SCLERAL DEPRESSOR

(75) Inventors: Timothy W. Olsen, Atlanta, GA (US); Paul E. Loftness, Gibbon, MN (US); Arthur G. Erdman, New Brighton, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 799 days.

(21) Appl. No.: 12/194,377

(22) Filed: Aug. 19, 2008

(65) Prior Publication Data
US 2009/0171364 A1 Jul. 2, 2009

Related U.S. Application Data

(63) Continuation of application No. 10/735,268, filed on Dec. 12, 2003, now Pat. No. 7,419,493.

(60) Provisional application No. 60/433,119, filed on Dec. 13, 2002, provisional application No. 60/466,630, filed on Apr. 30, 2003.

(51) Int. Cl.
*A61F 9/00* (2006.01)
(52) U.S. Cl. ........................................ 606/107; 600/236
(58) Field of Classification Search .............. 606/1, 107, 606/205, 211; 600/201, 207, 209, 213, 214, 600/219, 231, 225, 227, 232, 236
See application file for complete search history.

(56) References Cited

U.S. PATENT DOCUMENTS

| | | | |
|---|---|---|---|
| 2,438,646 A | 3/1948 | Pulliam | |
| 2,885,537 A | 5/1959 | Wood, Jr. | |
| 3,503,397 A | 3/1970 | Fogarty et al. | |
| 3,680,546 A | 8/1972 | Asrican | |
| 4,300,564 A | 11/1981 | Furihata | |
| 4,453,546 A | 6/1984 | Katz et al. | |
| 5,054,906 A | 10/1991 | Lyons, Jr. | |
| 5,171,254 A | 12/1992 | Sher | |
| 5,181,922 A | 1/1993 | Blumenkanz et al. | |
| 5,359,995 A | 11/1994 | Sewell, Jr. | |
| 5,366,474 A | 11/1994 | Blumenkanz et al. | |
| 5,688,264 A | 11/1997 | Ren et al. | |
| 5,865,832 A | 2/1999 | Knopp et al. | |
| 5,947,958 A | 9/1999 | Woodard et al. | |

(Continued)

FOREIGN PATENT DOCUMENTS
WO WO-9302624 A1 2/1993
(Continued)

OTHER PUBLICATIONS
"U.S. Appl. No. 10/735,268, Notice of Allowance mailed Apr. 29, 2008", NOAR, 6.
(Continued)

*Primary Examiner* — Kevin T Truong
(74) *Attorney, Agent, or Firm* — Schwegman, Lundberg & Woessner P.A.

(57) ABSTRACT

A remotely controllable system and method for positioning and operating a scleral depressor. A track is positioned to encircle at least a portion of the eye. One or more independent thrusters, or actuators, are radially positionable about the eye. An actuator is selectively deployable and selectively retractable by remote control. Thrusters may be mechanically operated and include pneumatic, hydraulic, electrical, chemical or other power supply forces. Remote control is provided by hand-operated controls, foot-operated switches or voice-operated control. A light source is positioned about at least a portion of the eye to provide transcleral illumination.

7 Claims, 18 Drawing Sheets

U.S. PATENT DOCUMENTS

| | | | |
|---|---|---|---|
| 5,971,977 A * | 10/1999 | Korenfeld | 606/1 |
| 6,010,518 A | 1/2000 | Prywes | |
| 6,068,643 A | 5/2000 | Milverton | |
| 6,267,752 B1 | 7/2001 | Svetliza | |
| 6,283,913 B1 * | 9/2001 | Seibel | 600/236 |
| 6,309,374 B1 | 10/2001 | Hecker et al. | |
| 6,440,065 B1 | 8/2002 | Hered | |
| 7,175,594 B2 | 2/2007 | Foulkes | |
| 7,985,180 B2 * | 7/2011 | Brown | 600/236 |

FOREIGN PATENT DOCUMENTS

| | | |
|---|---|---|
| WO | WO-0191756 A2 | 12/2001 |

OTHER PUBLICATIONS

"U.S. Appl. No. 10/735,268, Amendment and Response filed Feb. 21, 2008 to Final Office Action mailed Jan. 22, 2008", 10.

"U.S. Appl. No. 10/735,268 Final Office Action mailed Jan. 25, 2008", FOAR, 7 pgs.

"EP 0597953A1, Supplementary Partial European Search Report", (Sep. 29, 1994), 9 pages.

"Non-Final Office Action mailed Aug. 16, 2007 in U.S. Appl. No. 10/735,268", OARN, 3.

Lesnoni, G, et al., "The use of panoramic viewing system in relaxing retinotomy and retinectomy", *Retina*, (17)3, (1997), 186-190.

Murray, T G, et al., "A technique for facilitated visualization and dissection of the vitreous base, pars plana, and pars plicata", *Arch Ophthalmolmol*, 109(10), (Oct. 1991), 1458-1459.

Townsend, W D, "Scleral depression", *Optom Clin.*, 2(3), (1992), 127-144.

Walters, G B, "The technique of scleral indentation", *J Am Optom Assoc.*, 53(7), (Jul. 1982), 569-573.

* cited by examiner

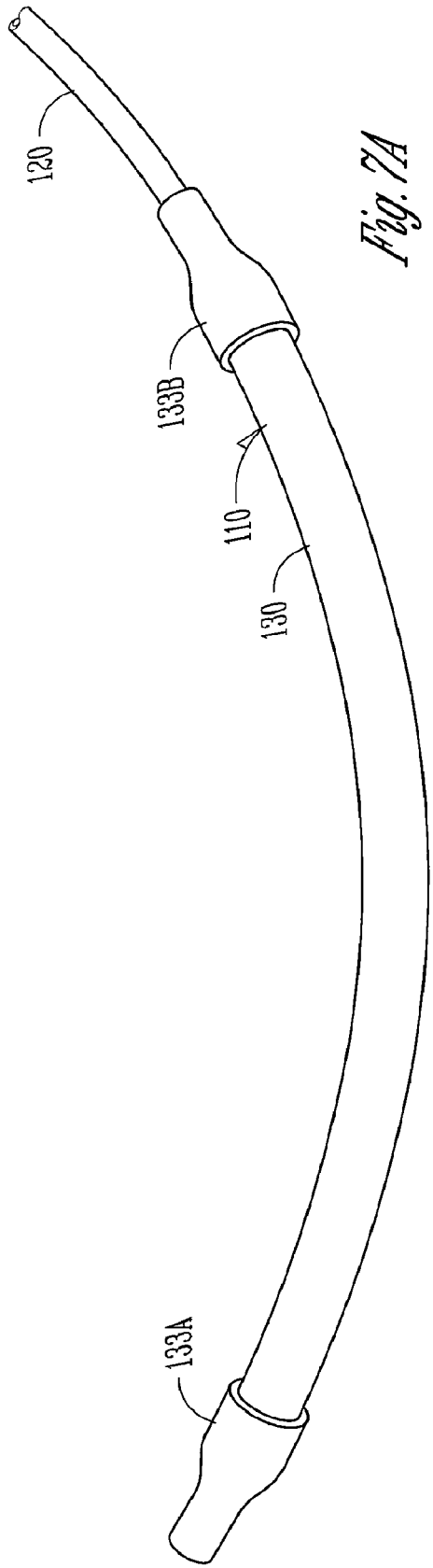
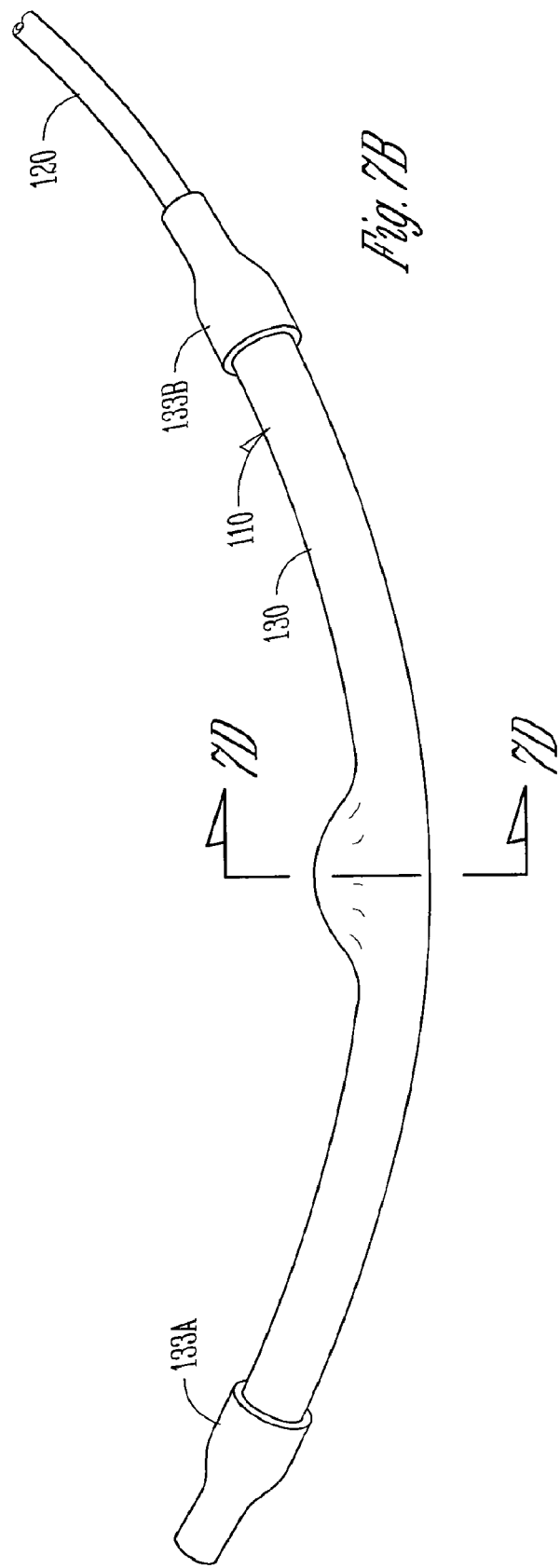
Fig. 7A
Fig. 7B

SCLERAL DEPRESSOR

RELATED APPLICATIONS

This application is a continuation of U.S. patent application Ser. No. 10/735,268, filed Dec. 12, 2003 now U.S. Pat. No. 7,419,493, which claims priority to U.S. Provisional Patent Application Ser. No. 60/433,119, entitled SCLERAL DEPRESSOR, filed Dec. 13, 2002 the entire specification of which is hereby incorporated by reference.

This document claims priority to U.S. Provisional Patent Application Ser. No. 60/466,630, entitled ILLUMINATED SCLERAL DEPRESSOR, filed Apr. 30, 2003, the entire specification of which is hereby incorporated by reference.

TECHNICAL FIELD

This invention relates generally to ophthalmic surgical and examination systems and methods, and particularly, but not by way of limitation, to a method of depressing the sclera.

BACKGROUND

Ophthalmic surgeries of the retina are often complicated by optical and physical barriers. For example, the anatomy and optical properties of the eye may obscure or obstruct the surgeon's view, particularly of the peripheral retina. The zone behind the iris (the colored portion of the eye) is obstructed from direct view. Consequently, the surgeon sometimes finds it helpful to have an assistant manually apply pressure or "depression" to the outside of the eye in order to bring the retina into adequate view to facilitate surgical manipulation.

Exemplary surgical techniques for which depression of the sclera may be helpful include removal of scar tissue and peripheral vitreous, laser photocoagulation techniques, addressing retinal tears or breaks and others.

The technique of manually applying pressure to the eye is not without problems. Assistants may be inexperienced or unable to properly apply pressure to aid the surgeon in visualization of the important peripheral pathology. Unexpected movement by the assistant may also cause problems for the surgeon and may be dangerous.

Furthermore, poor lighting of the surgical field often leads to complications during delicate intraocular surgical procedures. For example, inadequate lighting often impairs identification of small peripheral retinal breaks or tears.

For these and other reasons, what is needed is a method and system to allow a surgeon to control application of pressure to the sclera and improve visualization of the peripheral retina.

SUMMARY

An automated scleral depression system provides remote control of a scleral depressor. The scleral depressor can be positioned and actuated by a surgeon or assistant. In one embodiment, a foot operated control is coupled to a depressor and allows specific control of an actuator or light. In one embodiment, a hand operated control is coupled to a depressor and allows specific control of an actuator or light. In one embodiment, a voice operated control is coupled to a depressor and allows specific control of an actuator or light. In one embodiment, a microphone is coupled to a processor and voice commands are used to direct the positioning and actuation of the scleral depressor or light. In one embodiment, a flexible cable is used to direct the positioning and actuation of the scleral depressor or light.

The present subject matter allows lateral displacement, or depression, of the wall of the eye to facilitate surgical procedures. A thruster, or depressor component, provides the lateral mobilization. In one embodiment, a remote control allows selection of the radial position of one or more thrusters. In one embodiment, a remote control allows selection of lateral mobilization of a selected thruster.

In one embodiment, a thruster is deployed, or retracted, by applying a rotational force to a shaft within a lumen encircling at least a portion of an eye and the thruster is radially positioned by extracting, or inserting, the shaft within the lumen. In one embodiment, deployment and retraction are controlled by extracting or inserting a shaft within the lumen and radial position is controlled by rotating the shaft.

This summary is intended to provide a brief overview of some of the embodiments of the present system, and is not intended in an exclusive or exhaustive sense, and the scope of the invention is to be determined by the attached claims and their equivalents.

BRIEF DESCRIPTION OF THE DRAWINGS

In the drawings, like numerals describe substantially similar components throughout the several views. Like numerals having different letter suffixes represent different instances of substantially similar components.

FIG. 7A illustrates a balloon type thruster sheathed in a protective sleeve.

FIG. 7B illustrates a deployed balloon type thruster.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

An axis directed from anterior to posterior and passing through the center of the eye is referred to herein as the longitudinal axis. Distances from the longitudinal axis are described as having a lateral position. Radial position refers to orientation about the longitudinal axis. Thus, if the eye is considered to be at the center of a clock face, each of the twelve hour marks has a different radial position, all having the same lateral distance from the longitudinal axis, herein represented by the shaft on which the clock hands are affixed. For example, the nose side of the right eye can be referred to as the 3 o'clock position. At any particular clock hour (or radial) position, a thruster can be extended to a high depression position meaning that the lateral dimension from the thruster to the longitudinal axis is small. In addition, a low depression position refers to a greater lateral dimension between the thruster and the longitudinal axis. Radial extension refers to a lateral dimension along a particular radial.

Figure 1A:
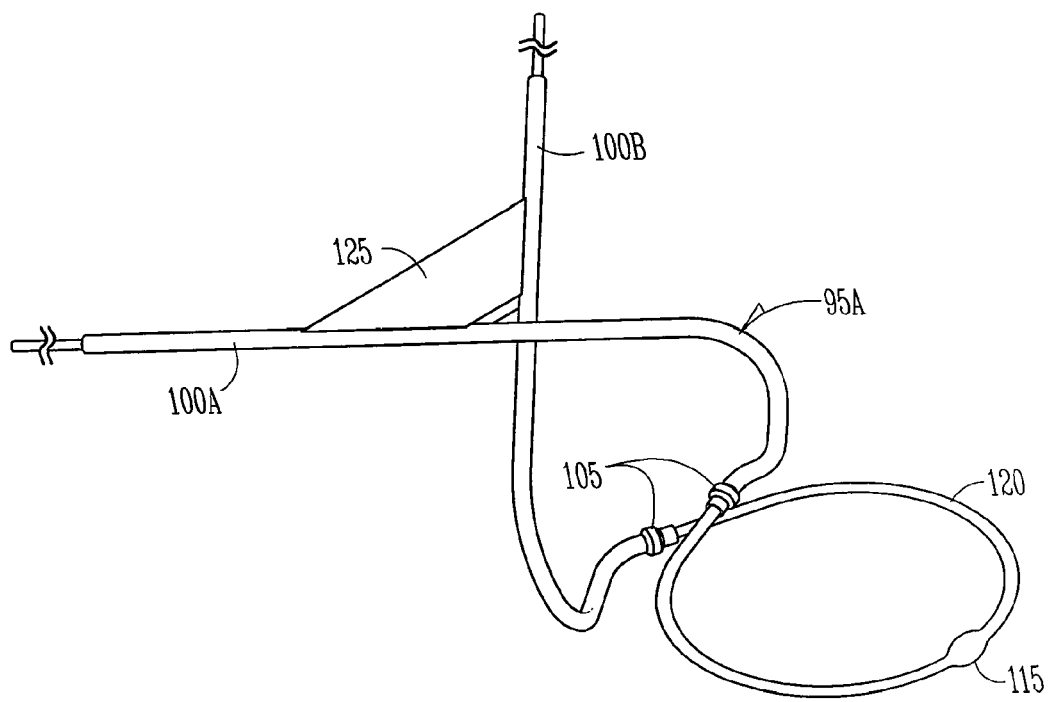
FIG. 1A illustrates an introducer fitted with a tube according to one embodiment of the present subject matter.

FIG. 1A illustrates a perspective view of introducer 95A adapted for use with one or more thrusters in accordance with one embodiment of the present subject matter. Legs 100A and 100B are tubular and joined by welded strut, or plate 125. In one embodiment, legs 100A and 100B are fabricated of stainless steel and plate 125 is fabricated of stainless steel sheet metal. In one embodiment, a nipple 105 is fixed to an end of each of legs 100A and 100B. In one embodiment, legs 100A and 100B are coupled together with a flexible joint to allow the legs to be individually manipulated to facilitate introduction of a track, or curvilinear guide, about the bony orbit of the eye.

Introducer 95A facilitates introduction of a track, or ring, around at least a portion of the eye, or globe. The track includes one or more curvilinear guide that at least partially encircle the eye. In one embodiment, the track includes an internal tube having a slot and a protective outer sheath or sleeve. One or more thrusters are positioned within the track as described more fully elsewhere in this document. In FIG. 1A, internal tube 120 is looped and threaded through the lumen of both leg 100A and leg 100B. In the figure, a single loop is illustrated, however, additional loops may also be used. In various embodiments, the placement of a thruster or light source about the bony orbit of the eye is guided by either tube 120 or track 110. Balloon 115 is shown to be inflated in the figure.

Figure 1B:
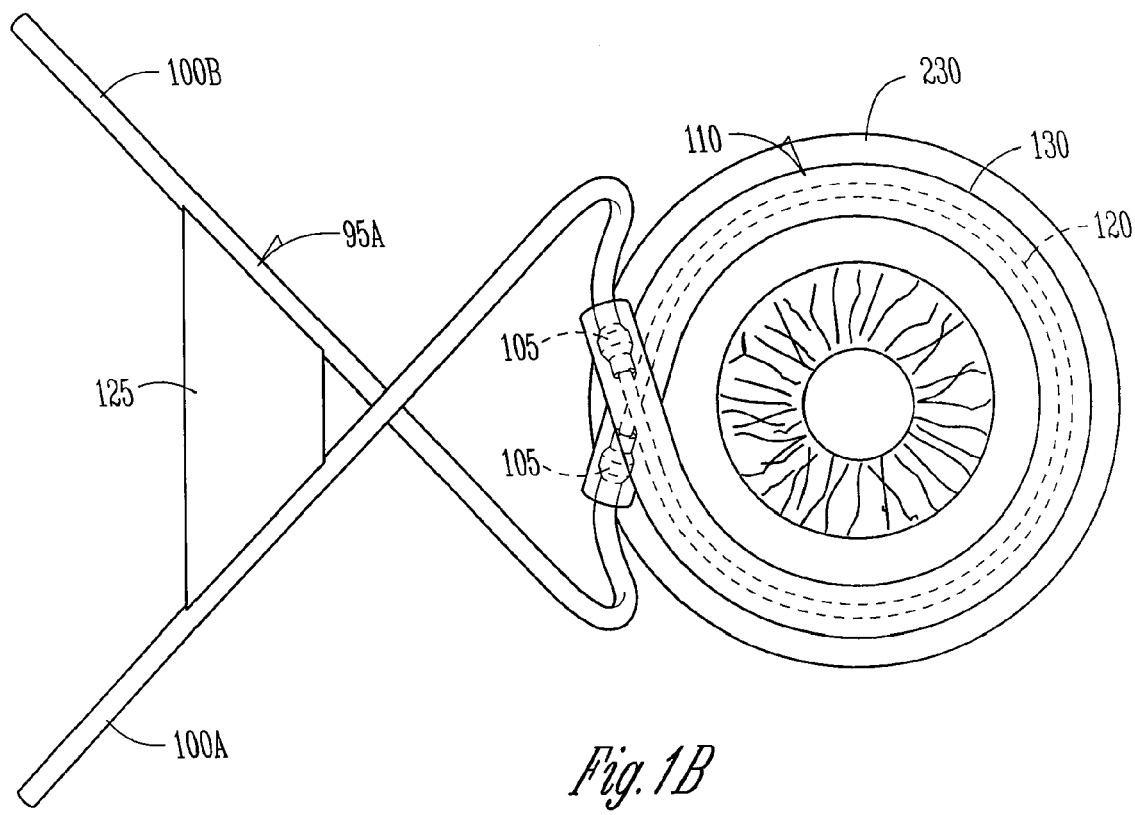
FIG. 1B illustrates an introducer fitted with a sleeve and positioned about an eye.

In one embodiment, nipple 105 is adapted to receive an end of track 110, as shown in FIG. 1B. Track 110, in the embodiment illustrated, includes a plastic tubular ring. Track 110, when positioned for use, encircles some or all of eye 230. According to one embodiment, tube 120 is positioned within the lumen of both legs 100A and 100B. In the embodiment shown, both ends of track 110 are accessible for coupling via legs 100A and 100B.

Alternative materials and structures are also contemplated for introducer 95A. For example, in one embodiment, introducer 95A is fabricated of a single formed tube rather than of two tubes. In one embodiment, introducer 95A is fabricated of molded plastic material having a pair of tubular guides arranged to facilitate introduction of track 110 as shown herein. In one embodiment, a single pneumatic coupling is provided for inflating a balloon within track 110 and the balloon is deflated by removing the air pressure supply. In one embodiment, plate 125 is secured to legs 100A and 100B by a mechanical fastener or a soldered or brazed connection. In one embodiment, introducer 95A is fabricated of a plastic, synthetic or other nonmetallic material. In one embodiment, nipples 105 are omitted and track 110 is coupled directly to legs 100A and 100B.

In one embodiment, tube 120 is used to both position and inflate balloon 115. In one embodiment, balloon 115 is joined or spliced onto tube 120 by a heat shrink tubing, an adhesive or other coupling means. In one embodiment, balloon 115 is molded into position during the fabrication process of tube 120. Balloon 115 can be positioned at an end of tube 120 or positioned in the middle of tube 120. In one embodiment, tube 120 is positionable within the lumen of track 110 and track 110 is covered with protective sleeve 130.

FIG. 1B illustrates a top view of introducer 95A coupled to protective sleeve 130 of track 110. Protective sleeve 130, in the figure, includes a transparent plastic tube. A slot in track 110 is not shown in FIG. 1B. In the figure, eye 230 is shown within the loop formed by sleeve 130.

Figure 2:
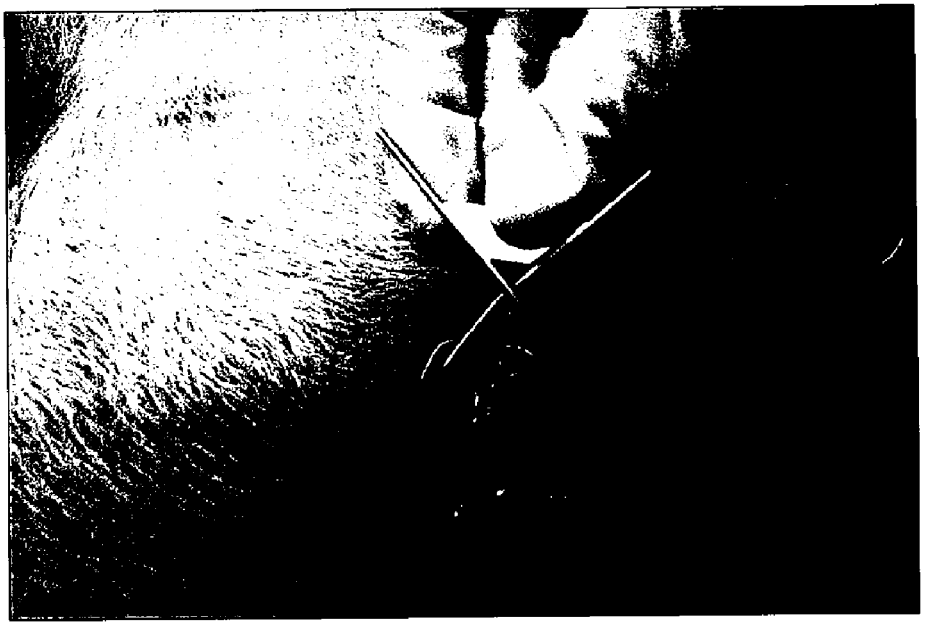
FIG. 2 illustrates an introducer positioned near a pig model eye.

In FIG. 2, introducer 95A is held in a position near the eye of a pig model. The figure illustrates relative sizes for one embodiment of the present subject matter.

Figure 3:
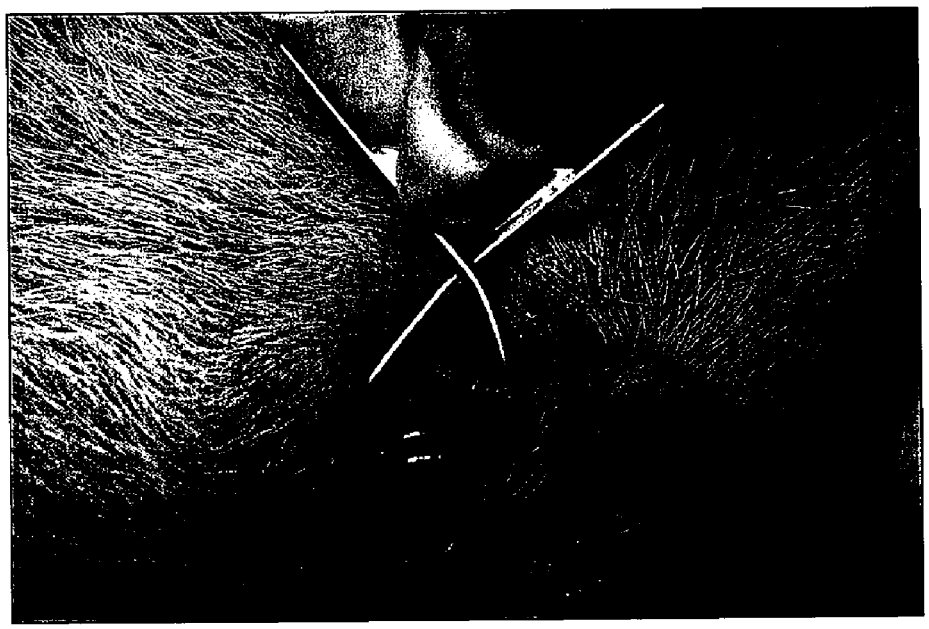
FIG. 3 illustrates an introducer positioned on a pig model eye.

In FIG. 3, introducer 95A is shown in a position in which track 110 encircles the pig model eye. As shown, nipples 105 and track 110 are positioned under the eyelids, and a portion of the introducer is located under the lateral canthus and is therefore, not visible in the figure.

Figure 4:
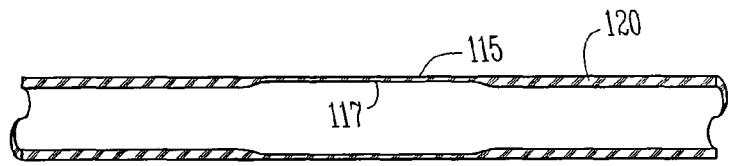
FIG. 4 illustrates a cut-away view of a balloon segment.
Figure 5:
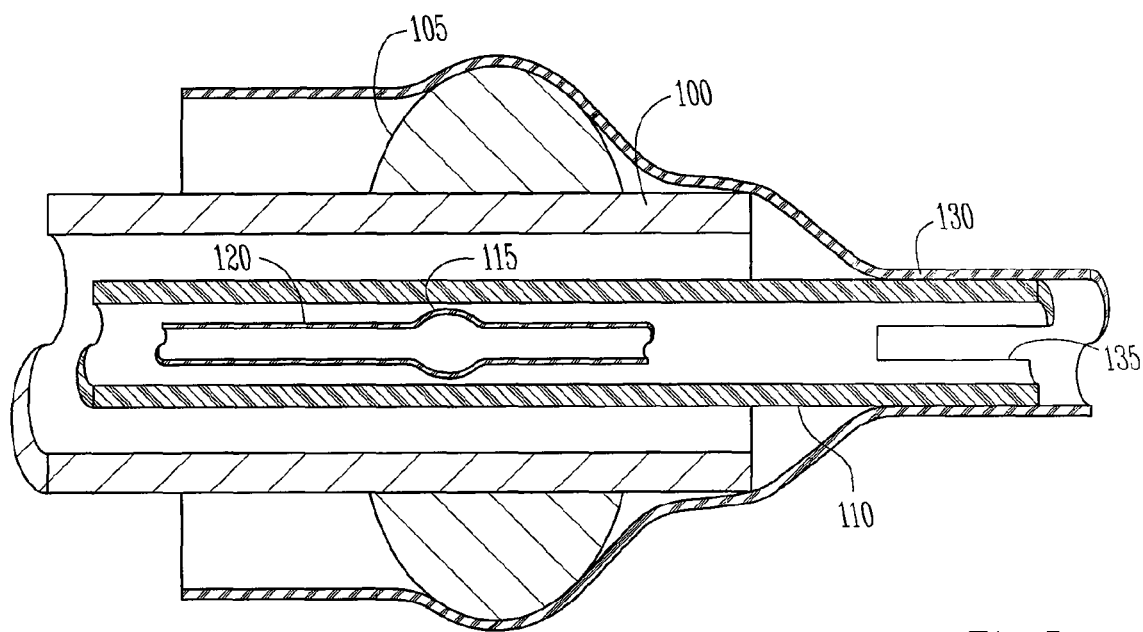
FIG. 5 illustrates a cut-away view of a track segment with a sleeve.

FIG. 4 illustrates a cross-section of a segment of a balloon in a length of tube 120 for use with the structure illustrated in FIG. 5. In FIG. 4, balloon 115 is fabricated of an elastic material such as rubber or latex and has a thin wall portion at 117. Thin wall portion 117 expands to a larger diameter when pressure is applied to the interior. For example, liquid or gas pressure may be applied to a first end of balloon 115 and vented or released at a second end of balloon 115. In one embodiment, balloon 115 includes a sealed envelope and pressure is applied and released from an orifice of balloon 115.

With respect to FIG. 5, a half section view of portions of track 110, according to one embodiment, is shown. In the figure, leg 100 is terminated with a nipple 105, herein illustrated as a bead or collar. Within leg 100 is track 110 having linear slot 135 of variable aperture. Track 110 is sheathed within the lumen of sleeve 130 and sleeve 130 is affixed, by nipple 105, to leg 100. In the embodiment shown, leg 100 is fabricated of substantially rigid plastic or tubular shaped metal. Nipple 105, in one embodiment, includes a raised bead formed in the end of leg 100 or is fabricated of other material such as metal or plastic. Track 110 is fabricated of plastic such as Teflon® (E.I. du Pont de Nemours and Company, Wilmington, Del.), polymeric compound or other semi-rigid material. Sleeve 130 is fabricated of an elastic material such as rubber, latex or other thin polymer and in the embodiment shown, is held in position by a friction fit over nipple 105. In one embodiment, sleeve 130 is held in position by a length of heat shrinkable tubing.

In FIG. 5, tube 120 is disposed within track 110. Tube 120 includes balloon 115 and in the figure, balloon 115 is shown partially inflated and located in a region not encompassed by slot 135. Further insertion of tube 120 into track 110 brings slot 135 and balloon 115 into alignment.

In addition, the embodiment illustrated in FIG. 5 indicates that track 110 is routed within the lumen of leg 100 and sleeve 130 is fitted over nipple 105. In contrast to the embodiment of FIG. 5, the embodiment of FIG. 1B shows track 110 is fitted over nipple 105 and tube 120 is positioned within the lumen of legs 100A and 100B. Other configurations for the relative orientation of coupling track 110, tube 120, sleeve 130 and legs 100 are also contemplated.

Introducer 95A facilitates the installation of track 110 at a position encircling at least a portion of the eye. Track 110 is positioned in a manner such that slot 135 is adjacent to the area of the eye that is to be depressed. In one embodiment, slot 135 is of a length that encircles a portion of the eye. In one embodiment, slot 135 is of a length that encircles the eye one or more times. Multiple loops around eye 230 permit a particular thruster to be positioned at one of two or more positions along the longitudinal axis.

Figure 6:
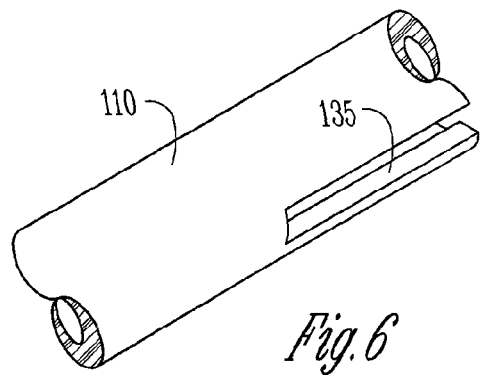
FIG. 6 illustrates a slotted tube segment.

FIG. 6 illustrates an isometric view of a portion of track 110. Slot 135 is visible in the figure and provides extension space into which balloon 115 expands when inflated or otherwise pressurized. Thus, in one embodiment, track 110 is aligned such that slot 135 is directed towards the longitudinal axis of the eye.

In FIG. 7A, sleeve 130 is illustrated having protective ends 133A and 133B. Sleeve 130, in one embodiment provides a physical barrier between thin wall section 117 and the eye. Ends 133A and 133B, in one embodiment, include heat shrinkable tubing. Tube 120 is illustrated to be disposed in the lumen of track 110, which is also disposed in the lumen of sleeve 130, and extending beyond one end. In FIG. 7B, track 110 is shown with a deployed thruster. In the figure, a pneumatic thruster is pressurized and a thinned portion, such as shown at 117 (FIG. 4), has expanded, resulting in a raised portion of sleeve 130.

Figure 7C:
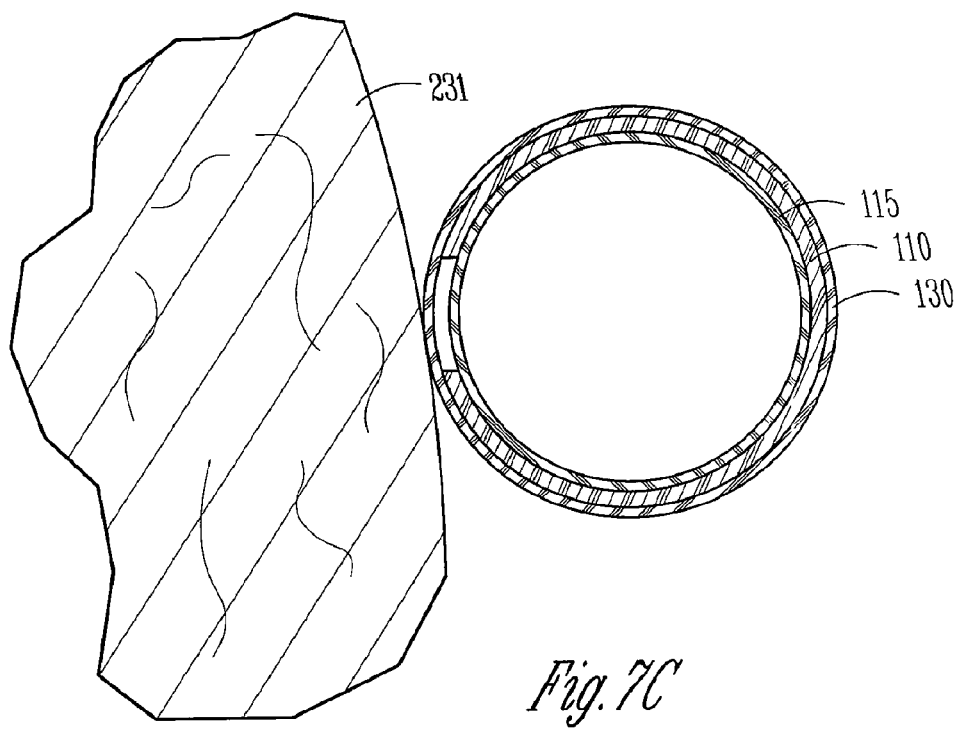
FIG. 7C illustrates a sectional view of a balloon type thruster in a deflated mode.
Figure 7D:
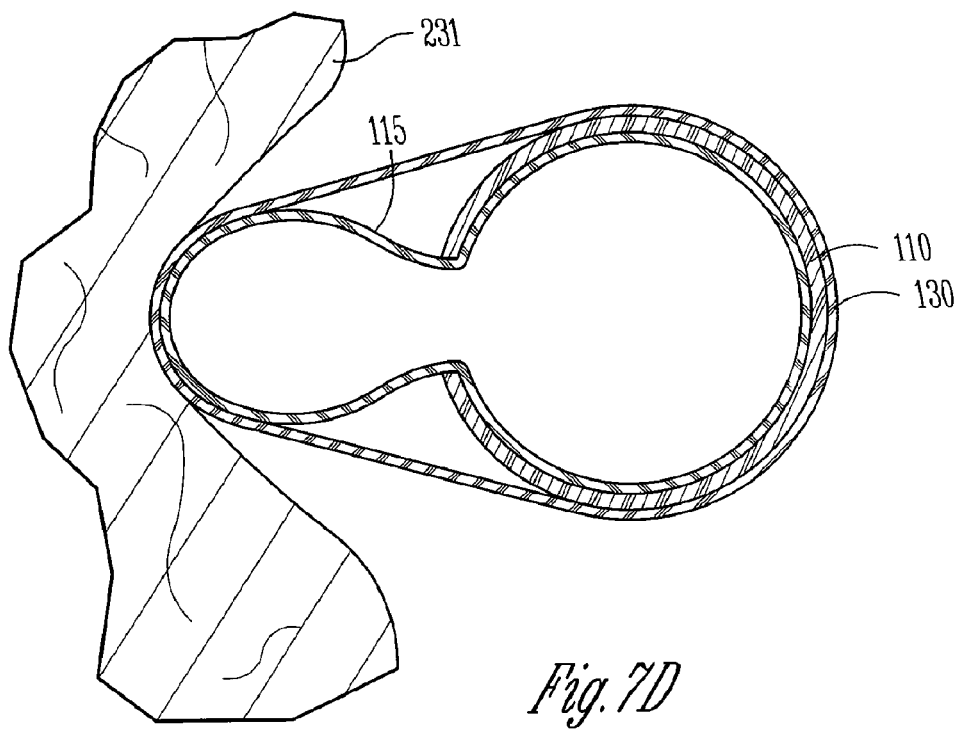
FIG. 7D illustrates a sectional view of a balloon type thruster in a deployed mode.

Sectional views of a balloon type thruster are shown in FIGS. 7C and 7D. In both FIG. 7C and FIG. 7D, the combination of track 110, tube 120 and sleeve 130 are positioned adjacent sclera 231 with the slot of track 110 directed towards sclera 231. In FIG. 7C, balloon 115 is substantially deflated and thus occupies the lumen of track 110. Protective sleeve 130 encases track 110. In FIG. 7D balloon 115 is inflated, as shown at cut line 7D-7D of FIG. 7B, and is forced out of the lumen by air pressure. Protective sleeve 130 expands to accommodate the increased size of balloon 115. Sclera 231 is depressed in the region adjacent the slot of track 110.

In one embodiment, the dimensions of slot 135 are selected to allow a thruster to exert a force to a predetermined portion of the eye. A particular width, length, placement, or shape of the aperture formed by slot 135 can be selected. In one embodiment, the aperture is circular or oval shaped. For example, with mature adults, a particular slot, or aperture dimension may be appropriate and for infants or youths, a smaller aperture may be appropriate for any given medical procedure.

In one embodiment, the amount of deployment, and thus, the force applied by a balloon type thruster can be selected by choosing the placement and dimensions of an aperture in track 110. For example, a larger aperture will allow a larger portion of a balloon to distend beyond the lumen of track 110.

Figure 8:
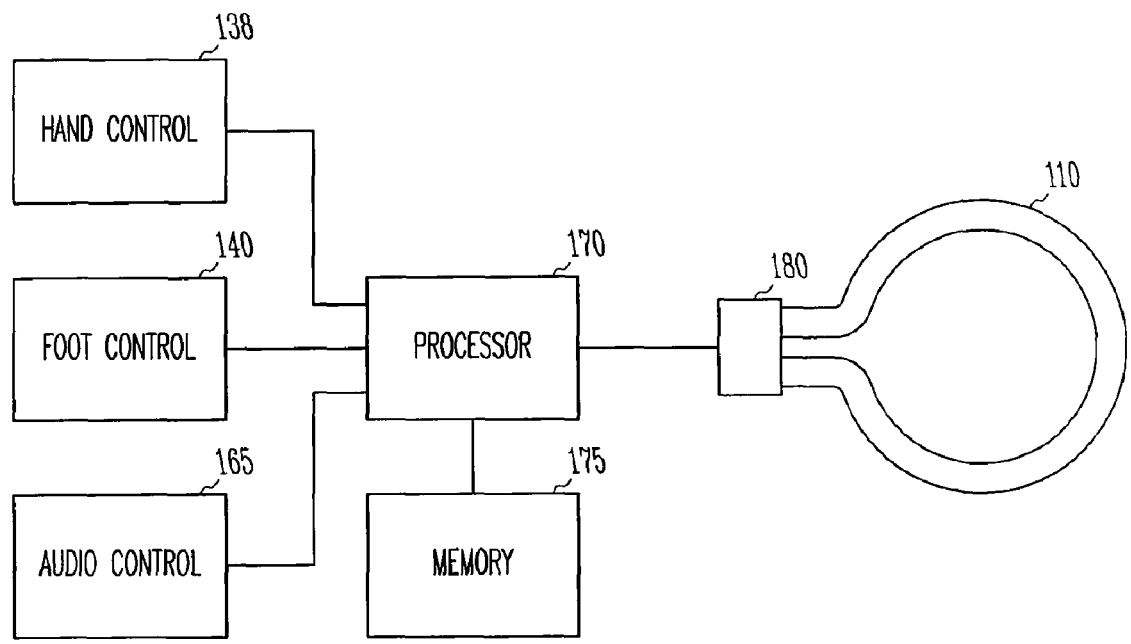
FIG. 8 schematically illustrates a foot control, audio control and hand control coupled to a processor controlled scleral depressor.

In FIG. 8, processor 170 is coupled to track 110 by interface 180. Track 110 includes one or more thrusters and one or more thruster positioning elements. Interface 180 includes hardware and programming to convert an electrical signal to mechanical motion to operate a thruster or to position a thruster. Processor 170 provides an electrical drive signal to interface 180. Processor 170 includes computer readable instructions and has access to memory 175. In one embodiment, hand control 138 is coupled to processor 170 and provides command signals for directing the operation of track 110. In one embodiment, foot control 140 is coupled to processor 170 and provides command signals for directing the operation of track 110. In one embodiment, audio control 165 is coupled to processor 170 and provides command signals for directing the operation of track 110. In one embodiment, a hand control 138, foot control 140, or audio control 165, permits independent control of the position of a thruster about the periphery of the eye as well as the amount of depression exerted by the thruster.

Hand control 138, in one embodiment, includes one or more user-operable controls for directing the operation of track 110. In one embodiment, a hand control includes a joy-stick type controller, a mouse, a touch-sensitive surface or one or more user-accessible switches.

Audio control 165, in one embodiment, includes a microphone, a processor and programming adapted to provide an electrical control signal based on a received verbal command. The control signal is received by processor 170 and, after further processing, provides a drive signal to interface 180.

Foot control 140, in one embodiment, includes one or more foot operable switches and includes programming adapted to provide an electrical control signal. The control signal is received by processor 170 and, after further processing, provides a drive signal to interface 180.

Figure 9:
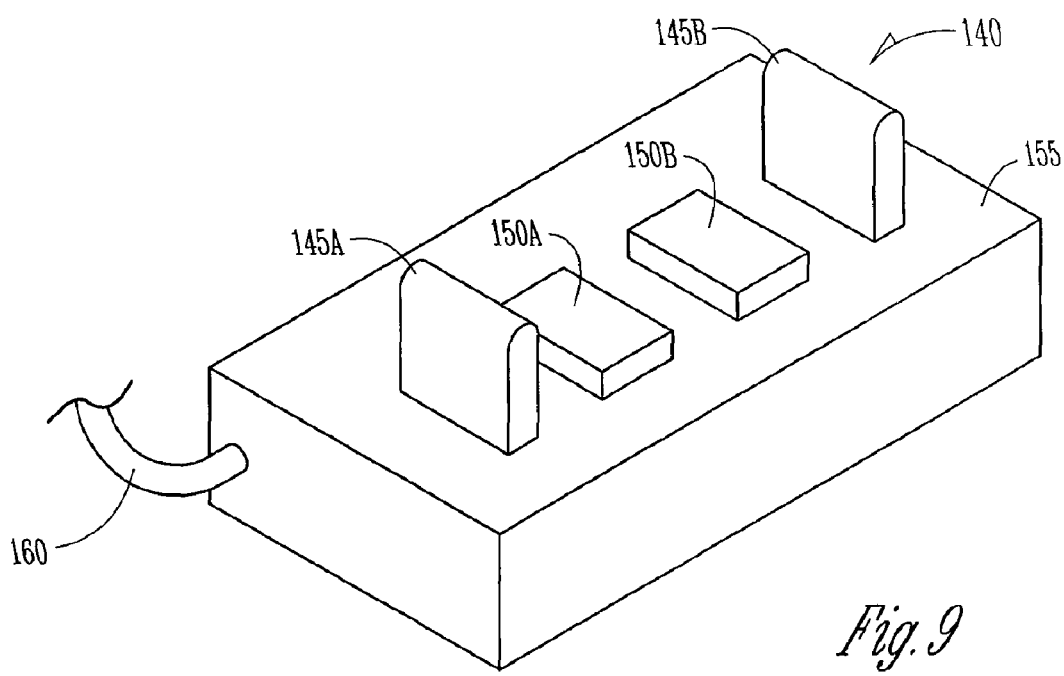
FIG. 9 illustrates a foot controller for position and displacement control of a particular thruster.

FIG. 9 illustrates foot controller 140 for operating a thruster according to one embodiment. Housing 155 includes electrical circuitry and is coupled to processor 170 by cable 160. Foot controller 140 includes positional switches 145A and 145B. When actuated, switches 145A and 145B, in one embodiment, rotate a particular thruster about the longitudinal axis in a clockwise and counter-clockwise direction, respectively. In one embodiment, positional switches 145A and 145B include toggle switches. Foot controller 140 also includes linear displacement switches 150A and 150B, actuation of which, in one embodiment, causes a particular thruster to be deployed or retracted by a predetermined linear distance. In one embodiment, by depressing and holding a linear displacement switch, the thruster commences movement and proceeds to retract or deploy to a predetermined linear position. In one embodiment, additional switches are provided to allow selective control over position and displacement of multiple thrusters.

Figure 10:
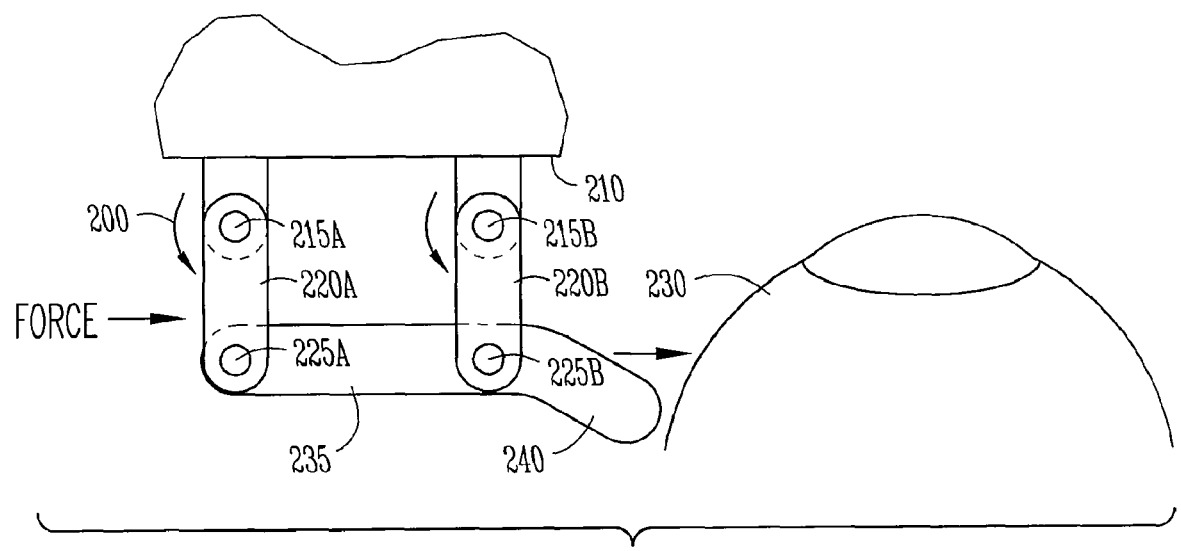
FIG. 10 schematically illustrates a thruster having articulating levers relative to an eye.

FIG. 10 illustrates one embodiment of a thruster according to the present system. In the figure, a first end of arm 220A is rotatably coupled to a boss secured to structure 210 and adapted to pivot about axis 215A. In addition, a first end of arm 220B is rotatably coupled to a boss secured to structure 210 and adapted to pivot about axis 215B. The second end of arm 220A and the second end of arm 220B are rotatably coupled to connecting link 235 and adapted to pivot about axis 225A and axis 225B. Contacting arm 240, in one embodiment, is coupled to connecting link 235. Contacting arm 240, in one embodiment, is coupled to arm 220B. Contacting arm 240 is brought into contact with eye 230 by applying a force in the direction of arrow 200. In one embodiment, the force is exerted by a rotating shaft coupled to a pivot axis such as 215A, 215B, 225A or 225B. In one embodiment, the force is exerted by a linear force applied to any of arm 220A, 220B or link 235. Arms 220A and 220B and link 235 are fabricated of a metal alloy or polymer material.

Figure 11:
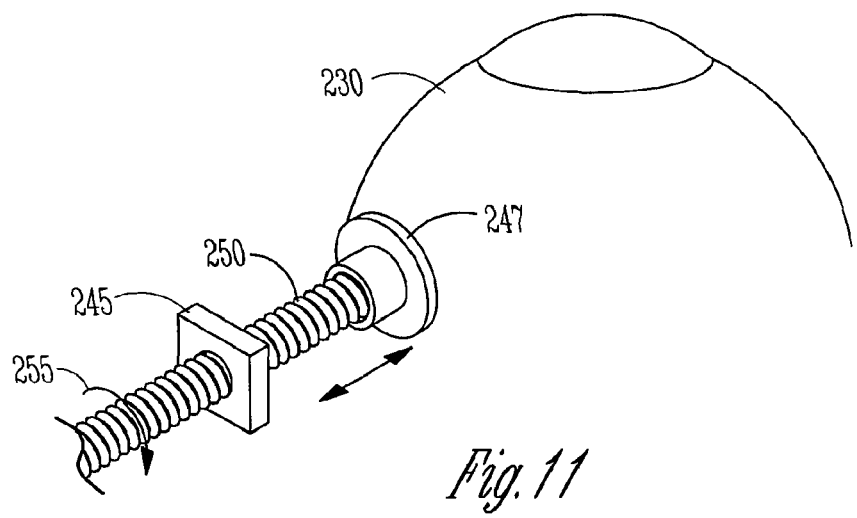
FIG. 11 schematically illustrates a threaded thruster relative to an eye.

FIG. 11 illustrates one embodiment of a thruster according to the present system. In the figure, rotatable shaft 250 has external threads which engage corresponding internal threads of stationary nut 245. Protective cap 247 is fitted to one end of shaft 250 and is adapted to contact the surface of eye 230. Cap 247, in one embodiment, is fabricated of a polymer and is adapted to rotate independent of shaft 250. A rotational force applied in the direction of arrow 255 causes shaft 250 to withdraw from eye 230. A rotational force applied in the opposite direction of arrow 255 causes shaft 250 to approach eye 230, thus applying a depression force. Cap 247 is adapted to not rotate when brought into contact with eye 230. In one embodiment, shaft 250 is secured to prevent rotation and nut 245 is rotated to extend or retract shaft 250 relative to eye 230.

Figure 12:
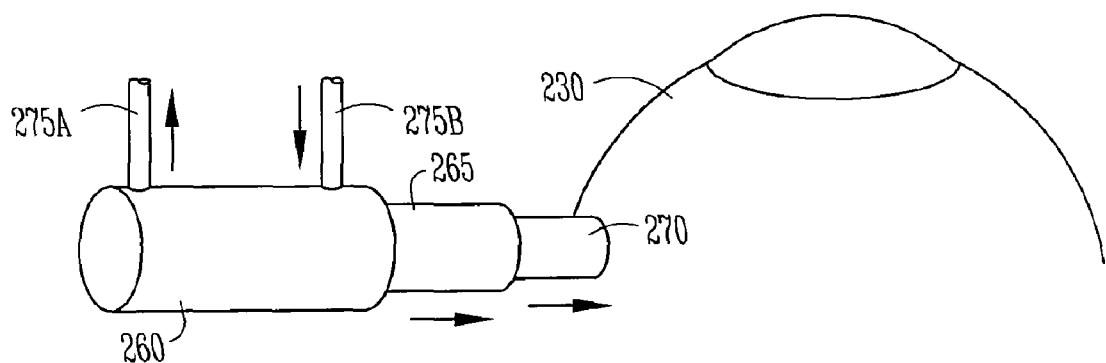
FIG. 12 schematically illustrates a telescoping cylinder thruster relative to an eye.
Figure 13A:
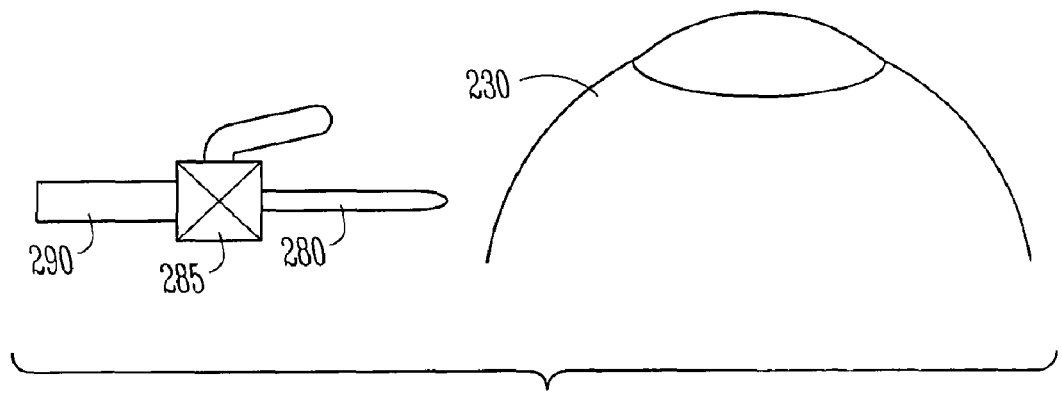
FIGS. 13A and 13B schematically illustrate an inflatable thruster relative to an eye.
Figure 13B:
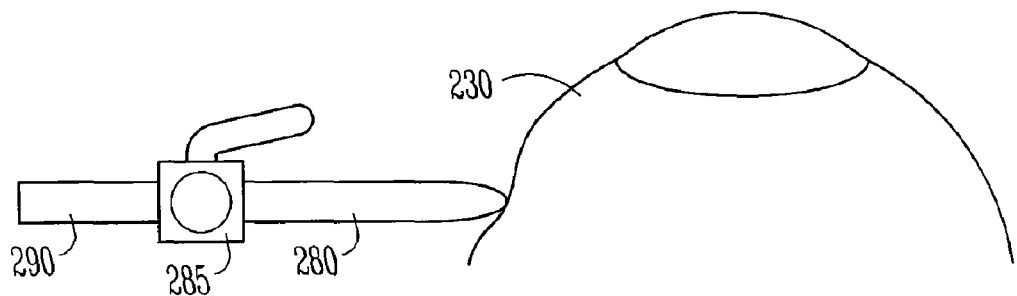

FIGS. 12, 13A and 13B illustrate embodiments having motive forces derived from a fluid pressure. Fluid pressure includes pneumatic pressure or hydraulic pressure. Pneumatic pressure refers to a pressure of a gas, some examples of which include air or an inert gas. Hydraulic pressure refers to a liquid pressure.

FIG. 12 illustrates one embodiment of a thruster according to the present system. In the figure, pushrod 270 is adapted to be received by an interior cavity of cylinder 265. The exterior dimensions of cylinder 265 are adapted to be received by an interior cavity of cylinder 260. Cylinder 260 is coupled to line 275A and line 275B. Cylinder 260, cylinder 265 and pushrod 270 are adapted for telescopic action. When pressure is applied using line 275B, cylinder 265 and pushrod 270 both move to an extended position. When pressure is removed from line 275A, cylinder 265 and pushrod 270 both move to a retracted position. In one embodiment, lines 275A and 275B are adapted to accept pneumatic pressure. In one embodiment, lines 275A and 275B are adapted to accept hydraulic pressure.

FIGS. 13A and 13B illustrate an embodiment of a thruster according to the present system. In FIG. 13A, for example, line 290 is coupled to a pressure supply. Line 290, in one embodiment, is coupled to a gas pressure line. Line 290, in one embodiment, is coupled to a fluid line. The fluid line can carry hydraulic or pneumatic pressure. Valve 285 is shown in a closed position and thus, balloon 280 is unpressurized. In FIG. 13B, for example, valve 285 is shown in an open position and thus, balloon 280 is pressurized and a force is exerted on a portion of eye 230. In one embodiment, a pair of lines are coupled to a balloon and pressurization of the balloon is controlled by introducing pressure via one line and relieving pressure via a second line. Other means of inflating, or pressurizing, a balloon are also contemplated.

Figure 14:
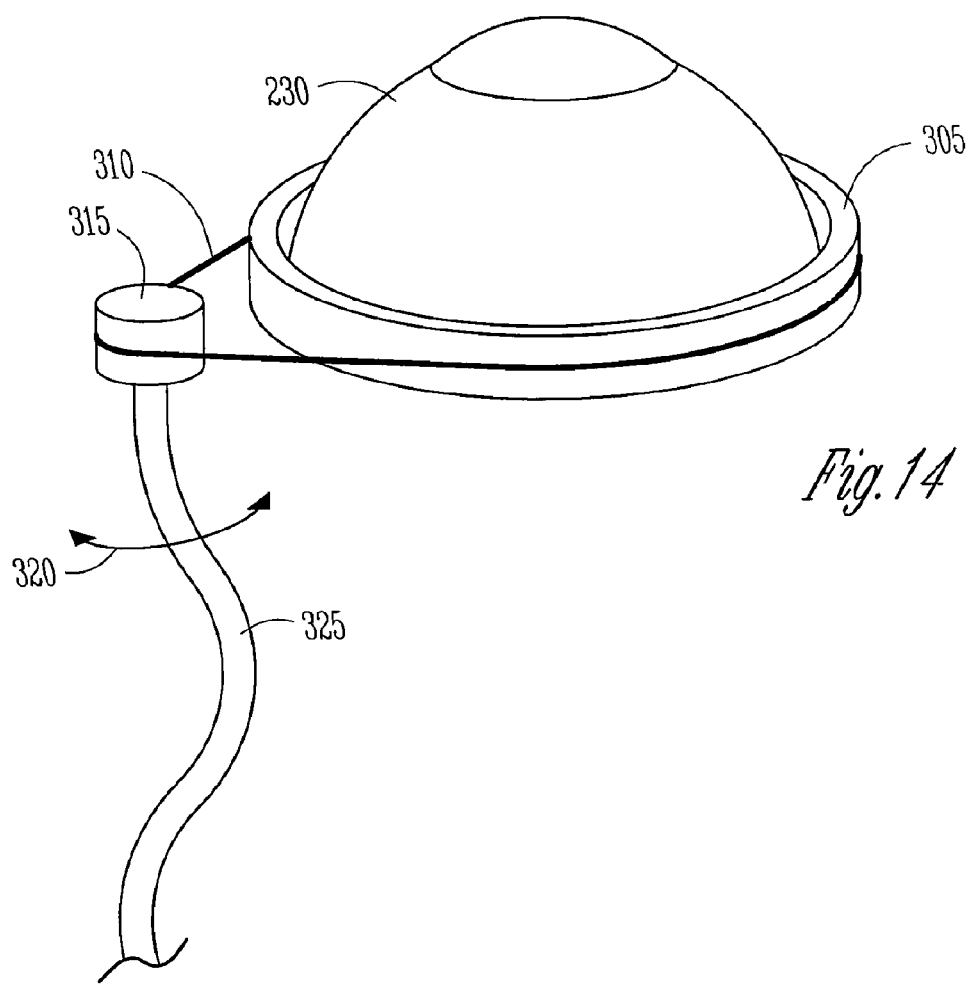
FIG. 14 schematically illustrates a flexible drive shaft operated radial positioning apparatus relative to an eye.

FIG. 14 illustrates one embodiment of a thruster positioning system according to the present subject matter. In the figure, eye 230 is encircled by driven ring 305. Driven ring 305 receives power from driving wheel 315 via cord 310. Driven ring 305 and driving wheel 315, in one embodiment, have a circumferential groove that receives cord 310. In one embodiment, teeth are located about the circumference of both driven ring 305 and driving wheel 315 and cord 310 includes a toothed belt. Flexible shaft 325 supplies rotational power to driving wheel 315 as illustrated, for example, by arrow 320. In one embodiment, a cord engages a take-up reel.

In one embodiment, one or more thrusters are coupled to driven ring 305. The radial position of the one or more thrusters is controlled by rotation of driven ring 305. In one embodiment, multiple concentric driven rings encircle the eye and one or more driving wheels are used to selectively position a particular thruster.

Figure 15:
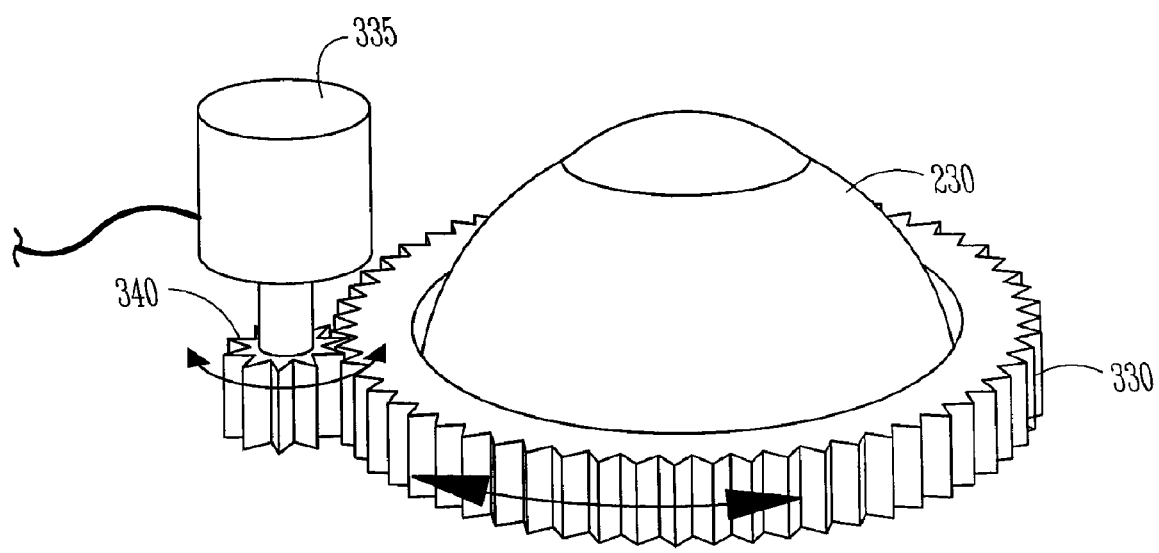
FIG. 15 schematically illustrates a ring gear and pinion drive operated radial positioning apparatus relative to an eye.

FIG. 15 illustrates one embodiment of a thruster positioning system according to the present subject matter. In the figure, eye 230 is encircled by ring gear 330. The sprockets of ring gear 330 engage pinion 340. Pinion 340 is driven by motor 335. In one embodiment, motor 335 includes a stepper motor. In one embodiment, pinion 340 is driven by a flexible shaft.

In one embodiment, a thruster is positioned by means of a friction drive. For example, a soft rubber wheel driven by a flexible shaft or stepper motor engages a ring encircling the eye. A thruster is coupled to the ring.

In one embodiment, one or more thrusters are coupled to ring gear 330. The radial position of the one or more thrusters is controlled by rotation of ring gear 330. In one embodiment, multiple concentric ring gears encircle the eye and one or more pinions are used to selectively position a particular thruster.

Figure 16A:
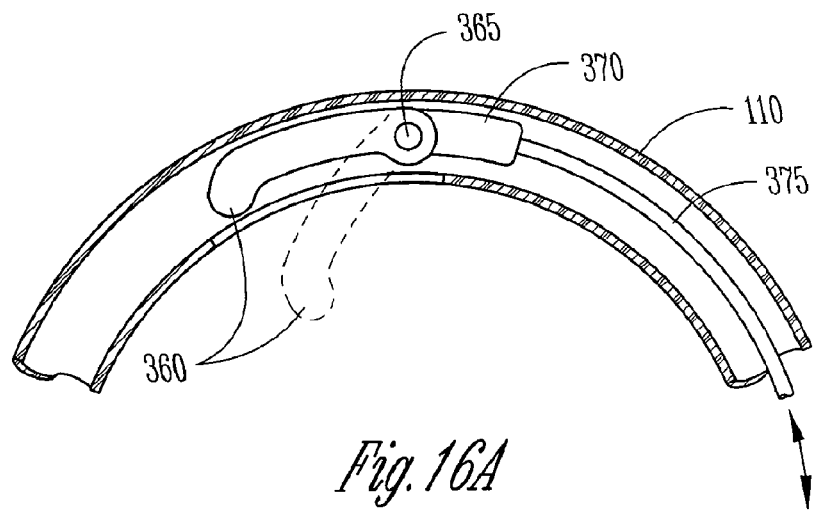
FIGS. 16A, 16B and 16C illustrate an articulating link thruster.
Figure 16B:
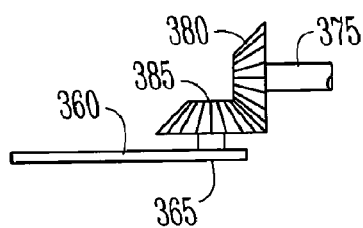

FIG. 16A and FIG. 16B illustrate a thruster according to one embodiment. In FIG. 16A, for example, thruster arm 360 is in a retracted position using a solid line and thruster arm 360 is shown in an extended, or deployed, position using a dashed line. Thruster arm 360 rotates about axis 365 which is coupled to transmission housing 370 having input shaft 375. In one embodiment, input shaft 375 is remotely accessible and allows control of the thruster. For example, thruster arm 360 can be radially positioned by pushing or pulling on shaft 375. In addition, arm 360 can be extended or retracted laterally by rotating shaft 375. In one embodiment, input shaft 375 is coupled to a mechanical drive system. Thruster arm 360, when retracted, is positioned within the lumen of track 110.

FIG. 16B illustrates apparatus for converting rotational forces on shaft 375 to a thruster force exerted by arm 360. Shaft 375 is coupled to arm 360 by driving bevel gear 380 and driven bevel gear 385. Other transmissions or gear trains are also contemplated. In one embodiment, gears 380 and 385 are enclosed within housing 370.

Figure 16C:
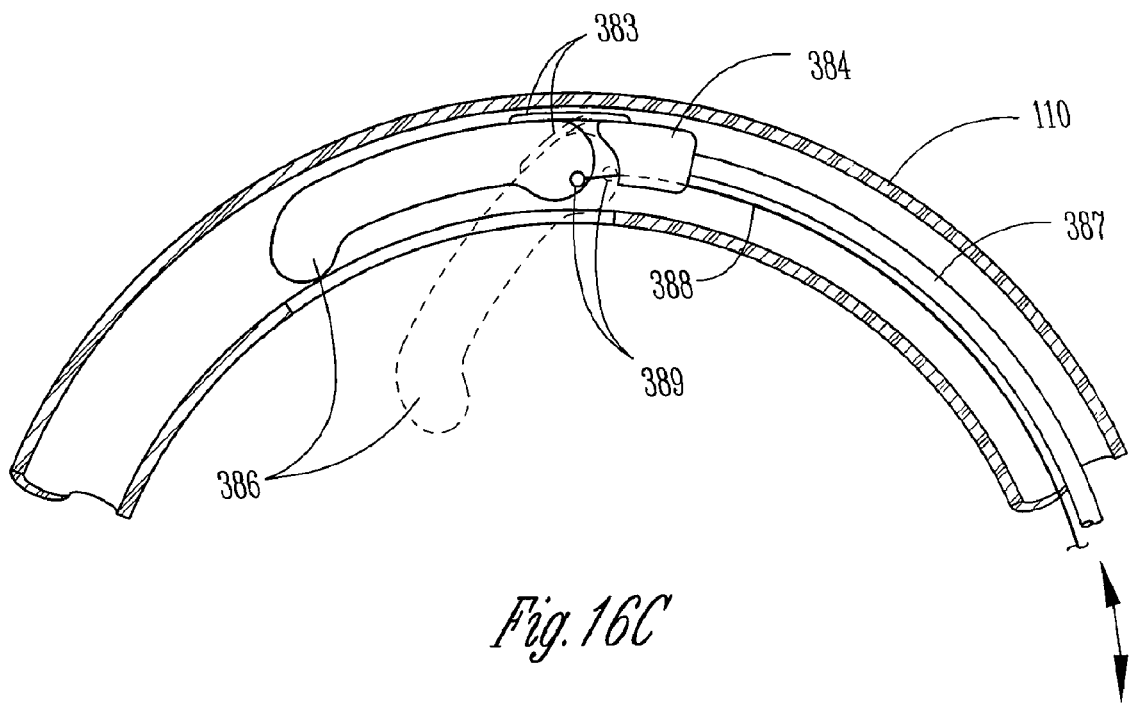

FIG. 16C illustrates a thruster according to one embodiment. Thruster arm 386 is depicted in the retracted position using a solid line and in the extended position using a dashed line. Thruster arm 386 is coupled to guide 384 by resilient strip 383. In one embodiment, shaft 387 extends beyond track 110 and is accessible externally. By pushing or pulling on shaft 387, thruster arm 386 can be positioned within track 110. Shaft 387, in one embodiment, includes a flexible shaft and may be fabricated of metallic or non-metallic material. Control line 388 is coupled to a portion of arm 386 and, in one embodiment, passes through a bore in guide 384, and extends beyond track 110 and is accessible externally. By pulling on control line 388, arm 386 is urged into an extended, or deployed position and when a pulling force is removed from control line 388, resilient strip 383 urges arm 386 into a retracted position. In one embodiment, arm 386, guide 384 and resilient strip 383 are configured to control movement of arm 386. In one embodiment, resilient strip 387 provides a return spring force to urge arm 386 into the retracted position.

Resilient strip 383, in various embodiments, includes a metallic or non-metallic leaf spring. In one embodiment, resilient strip 383 includes a live hinge and is fabricated of a polymer material. Resilient strip 383 is bonded or fastened to both guide 384 and arm 386. Control line 388, in one embodiment, includes a monofilament or polyfilament line.

Figure 17:
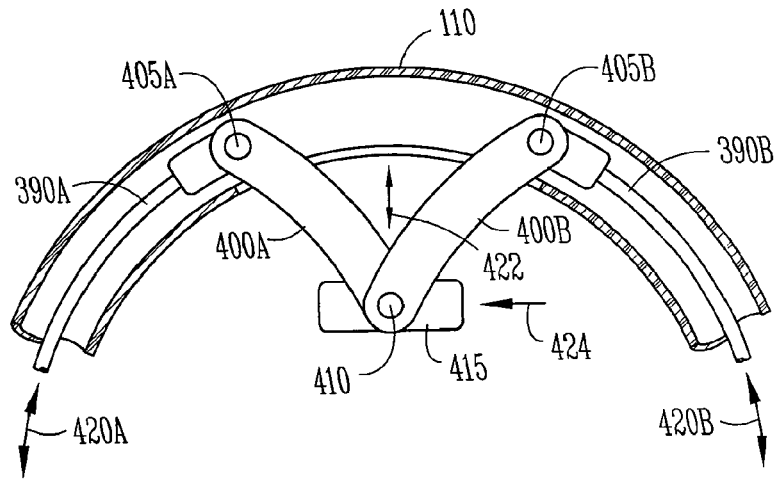
FIG. 17 illustrates a thruster having a two lever scissors arrangement.

FIG. 17 illustrates a thruster according to one embodiment. In the figure, arm 400A, arm 400B and thruster shoe 415 are linked together at pivot 410. Arm 400A is also coupled, at pivot 405A, to shaft 390A. Arm 400B is coupled, at pivot 405B, to shaft 390B. Shafts 390A and 390B are disposed in the lumen of track 110 and are remotely accessible. Arrows 420A and 420B indicate degrees of freedom for controlling the position and deployment of shoe 415. Shoe 415 is deployed and retracted by travel shown generally at arrow 422. For example, when either shaft 390A or shaft 390B, or both shafts 390A and 390B, are displaced in a generally downward direction, shoe 415 moves into a retracted position. To displace shoe 415 leftward in the figure, shaft 390A is displaced downwardly and shaft 390B is displaced upwardly. By manipulating shafts 390A and 390B, either independently or in combination, shoe 415 can be displaced radially as well as laterally. In one embodiment, shaft 390A is coupled to arm 400A by a transmission and arm 400B follows the motion of arm 400A. Thus, rotational forces on shaft 390A are translated to extension or retraction forces on arm 400A.

In one embodiment, a position of a thruster is controlled by manually manipulating a control cable or other flexible shaft. In one embodiment, deployment of a thruster is controlled by manually manipulating a control cable or other flexible shaft. For example, with regard to the embodiment of FIG. 17, braided wire ropes or cables coupled to shaft 390A and shaft 390B allow positioning of thruster shoe 415. In one embodiment, by pushing or pulling along the axis of the control cable, the position of a thruster can be adjusted or deployment of a thruster can be controlled. In one embodiment, rotation of the control cable adjusts the position of a thruster or deployment of a thruster.

Figure 18:
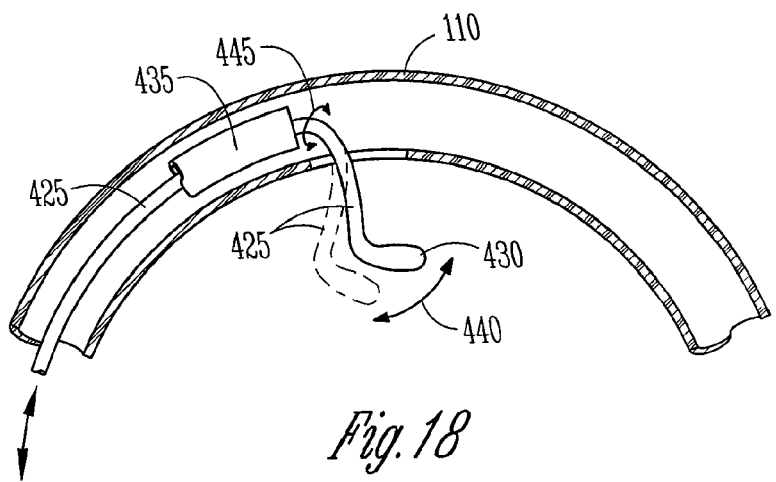
FIG. 18 illustrates a shape memory material thruster.

FIG. 18 illustrates a thruster according to one embodiment. In the figure, arm 425 terminates with foot 430. Foot 430 can be positioned to exert a depression force on the eye. In one embodiment, arm 425 can be manipulated, by rotation, as indicated by arrow 445, to exert an anterior, posterior or circumferential force on the eye. In addition, the elastic properties of arm 425 allow manipulation in directions as indicated by arrow 440. Arm 425 is accessible outside of the lumen of track 110. In one embodiment, arm 425 is fabricated of shape memory metal or shape memory material. Arm 425, in one embodiment, is adapted to retract into the lumen of track 110.

In one embodiment, super elastic properties of arm 425 allow specific thrust to be applied at a targeted area. For example, arm 425 can be rotated to exert thrust at a particular angle. In one embodiment, arm 425 is adapted to retract into the tube encircling the eye. Foot 430 can be deployed at a selected angle and can rotate anteriorly, posteriorly or circumferentially.

Figure 19A:
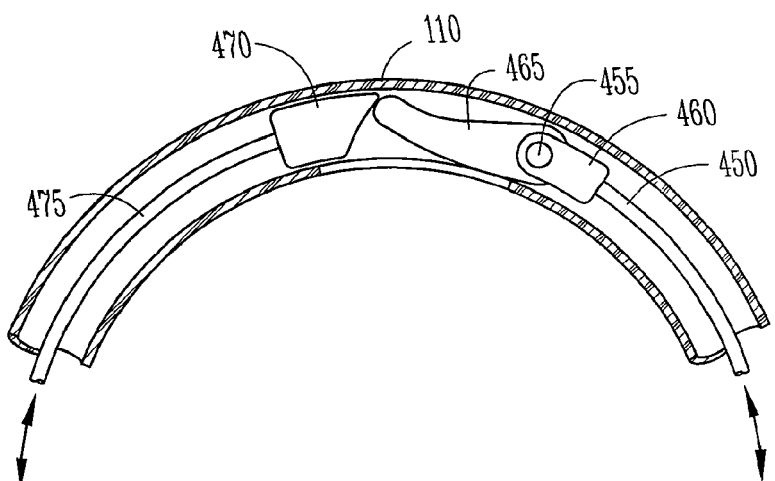
FIGS. 19A and 19B illustrate a cam actuated thruster.
Figure 19B:
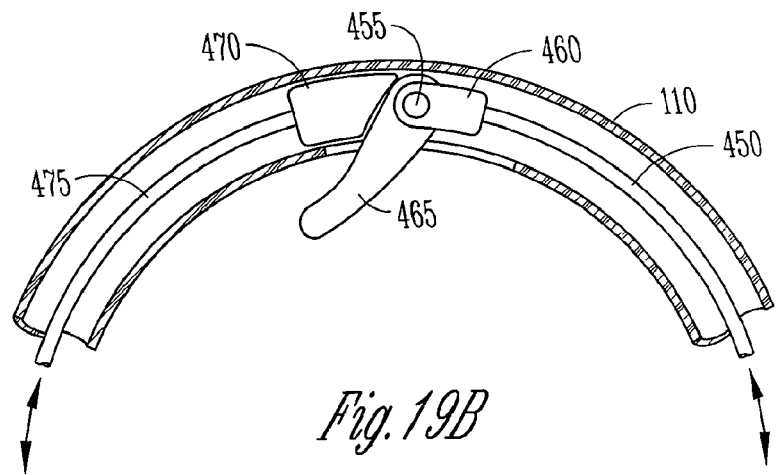

FIGS. 19A and 19B illustrate a cam operated thruster according to one embodiment. In the figure, thruster arm 465 is shaped to interface with a contour of cam 470. Cam 470 is remotely operable by way of shaft 475. Thruster arm 465 is linked to guide 460 at pivot 455. Cam 470 and guide 460 are sized to slidably fit within the lumen of track 110. Guide 460 is remotely operable by way of shaft 450. In FIG. 19A, thruster arm 465 is illustrated in a retracted position.

In FIG. 19B, thruster arm 465 is extended. In the figure, cam 470 and guide 460 have converged and a contour of cam 470 has forced thruster arm 465 into an extended position. A spring, or other force, acting on thruster arm 465 urges retraction of thruster arm 465 into the lumen of track 110. In one embodiment, a spring urges deployment of a thruster. Shafts 475 and 450 can be remotely manipulated to cause thruster arm 465 to be deployed at a particular location along the length of track 110. By adjusting the relative position of cam 470 and guide 460, the degree of extension or retraction of thruster arm can be controlled.

Figure 20:
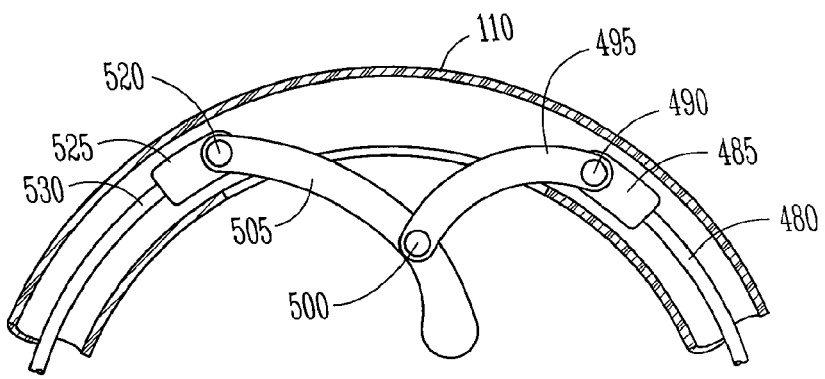
FIG. 20 illustrates a thruster having independently operable articulating mechanical links.

FIG. 20 illustrates a thruster according to one embodiment. In the figure, shaft 530 is coupled to guide 525. Guide 525 is coupled to a first end of arm 505 at pivot 520. Arm 505 is also coupled to a first end of arm 495 at pivot 500. A second end of arm 495 is coupled to guide 485 at pivot 490. Guide 485 is coupled to shaft 480. Guides 525 and 485 are sized to fit within the lumen of track 110. Shafts 480 and 530 are remotely accessible. A shaped end of arm 505 is adapted to exert a force on the eye. Arm 505 and arm 495, in one embodiment, have a curved shape with arm 505 longer than arm 495.

Arm 505 is retracted by increasing the distance between guide 525 and guide 485. Arm 505 is extended, or deployed, by reducing the distance between guide 525 and guide 485. In one embodiment, the radial position of the thruster in FIG. 20 is controlled by coordinated movement of guide 485 and guide 525.

To use one embodiment of the present subject matter, the track is assembled to the introducer. In assembling the track, a suitable remotely controlled drive is connected to any guides or shafts. The remotely controlled drive may include pneumatic, hydraulic or mechanical couplings. The track is then positioned about the eye using the introducer or other means of positioning. A thruster is positioned on, or within, the track at a desired location using the thruster positioning device. In one embodiment, a radial position for a thruster is selected after which the thruster is deployed. In one embodiment, a selected thruster is deployed and subsequently re-positioned. In one embodiment, multiple thrusters are independently positioned and deployed. In one embodiment, the track is placed within the bony orbit without the aid of introducer 95A.

Figure 21:
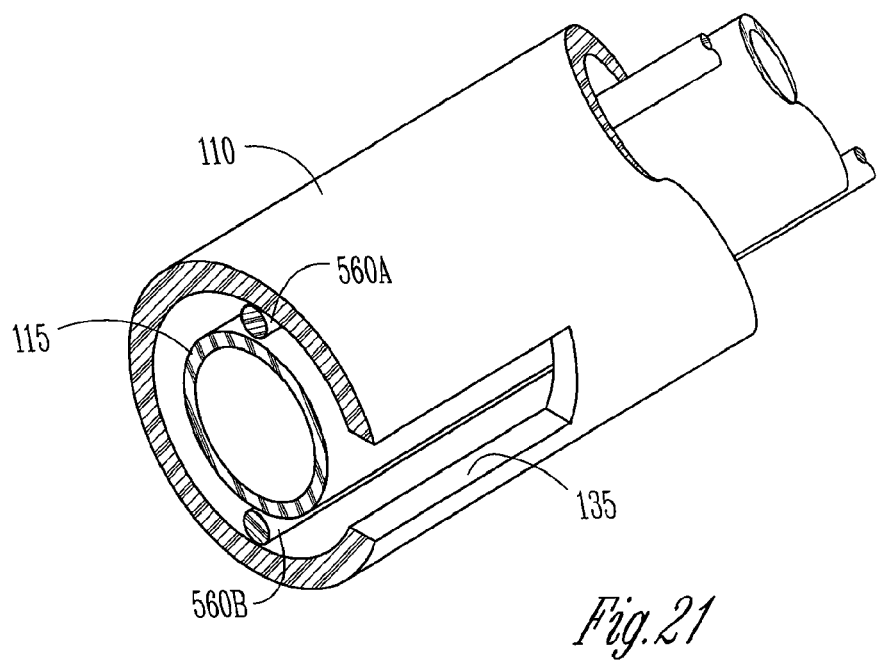
FIG. 21 illustrates a section view of a transcleral illuminator track.

In one embodiment, a light source, or illumination source, is positioned within track 110 to provide transcleral illumination. FIG. 21 illustrates an embodiment having two filaments within the lumen of track 110. In the figure, filament 560A and filament 560B are positioned alongside of balloon 115. In one embodiment, a single filament is disposed within the lumen of track 110. In one embodiment, a plurality of filaments are disposed within the lumen of track 110. In one embodiment, a filament is disposed within the lumen of balloon 115. In one embodiment, track 110 is fabricated of a transparent or translucent material. In one embodiment, protective sleeve 130 (not shown in the figure) is fabricated of transparent or translucent material. In one embodiment, the filament is positioned within track 110 by one of the systems and methods described elsewhere in this document. In one embodiment, an illumination source is disposed within a lumen of tube 120.

Each filament includes an optical element fabricated of glass or plastic and is sometimes referred to as a fiber optic filament. The filament is sufficiently flexible to conform to the routing of track 110. In one embodiment, the illumination source, filament, or light pipe, provides side illumination (side emitting). A coating on the filament allows light to diffuse from a side. When positioned around the eye, the side emitting light pipe provides diffuse illumination of the sclera.

In one embodiment, the illumination source or filament provides end illumination (end emitting). An end of the filament is treated to enhance light scattering. In one embodiment, the end is cut perpendicular and can be modeled as a point light source.

In one embodiment, an end emitting filament can be positioned within track 110 at a location independent of a thruster or balloon. In one embodiment, an end emitting filament is coupled to a thruster or balloon and is positioned within track 110 coincident with the positioning of the thruster or balloon. For example, in one embodiment, an end emitting filament is radially positioned to provide lighting opposite the position of the thruster or balloon. Multiple end-emitting filaments can be positioned within track 110. In one embodiment, an end emitting filament is positioned near one or both nipples of introducer 95A.

Figure 22:
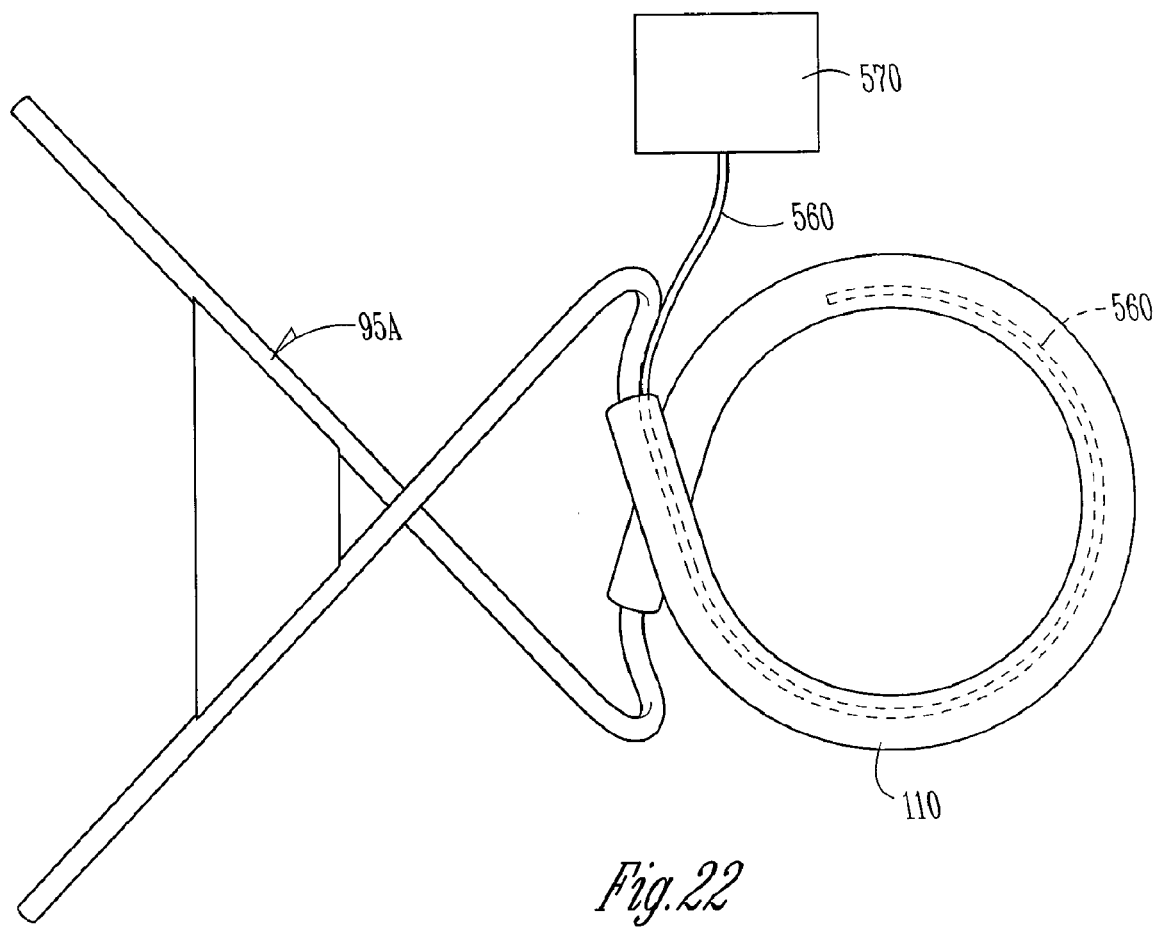
FIG. 22 illustrates a track coupled to a light source.

The filament is illuminated by remote light source 570 coupled to filament 560 as shown in FIG. 22. The remote light source includes a coupling to interface the filament with a light source. In one embodiment, the light source includes a plurality of light emitting diodes (LEDs). In one embodiment, the light source includes a halogen lamp.

In one embodiment, a track 110 or tube 120 is fabricated of material that provides illumination of selected portions of the eye. For example, in one embodiment, the track or tube includes a side emitting optical element that provides diffuse or focused lighting at a selected region of the eye. In one embodiment, the track is fabricated of a translucent material that conducts light to a particular portion. The light can be positioned or focused to illuminate a selected portion.

Alternative Embodiments

Variations of the above embodiments are also contemplated. For example, in one embodiment, a foot control or audio control allows operator selection of a thrust axis. The thruster can be configured to exert thrust along an axis normal to the longitudinal axis or at a particular angle to the longitudinal axis. For example, by rotating track 110, slot 135 can be repositioned and thus, balloon 115 exerts thrust at a selected angle to the longitudinal axis of the eye.

In one embodiment, a hydraulic or pneumatic force is used to position the thruster. For example, the thruster is coupled to a diaphragm or piston and hydraulic or pneumatic pressure (or vacuum) is applied to one end of a double acting cylinder. A double acting cylinder includes a shaft that extends from one end of a cylinder and is connected to a diaphragm or piston that moves in either direction within the cylinder under hydraulic pressure. Movement of the diaphragm or piston causes the thruster to be repositioned relative to the track. In one embodiment, the hydraulic fluid includes a saline solution.

In one embodiment, a thruster is coupled to a cable operated piston. Movement of the cable causes the thruster to be repositioned relative to the track. In one embodiment, a cord, filament, belt or other flexible device is used to position the thruster.

Figure 23:
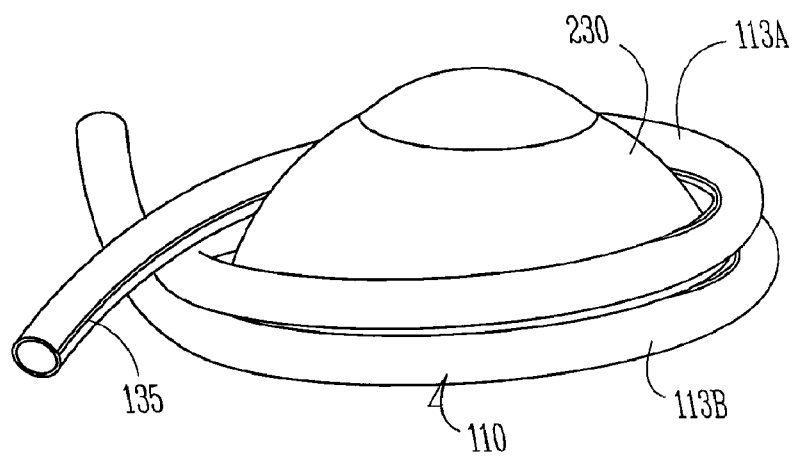
FIG. 23 illustrates a double loop track relative to an eye.

In one embodiment, a thruster can be positioned along one of two or more track segments that encircle the eye. For example, in one embodiment, a track includes a first loop and a second loop, as illustrated in FIG. 23, thus permitting depression of multiple anterior-posterior locations radially in the peripheral retina. As shown in the figure, track 110 includes an anterior portion 113A and a posterior portion 113B. Anterior portion 113A provides access to the pars plana region of eye 230, and posterior portion 113B provides access to the posterior vitreous base for surgery involving retinal detachment tears and circumferential contracture of the vitreous. Slot 135 is oriented towards the eye in the figure.

In the figure, anterior portion 113A and posterior portion 113B are contiguous. In one embodiment, anterior portion 113A is discontinuous with posterior portion 113B. In one embodiment, two or more portions of a track are provided. In one embodiment, multiple loops around the eye are sheathed in a single protective sleeve.

In one embodiment, the thruster is supported by the bony orbit of the eye and the track is captivated by the anterior orbital rim. In one embodiment, a bridge assembly couples the introducer to the nose of a patient. In one embodiment, the track and thruster are adapted for attachment to the blade of an eyelid speculum. In one embodiment, the track and thruster are integrated with an eyelid speculum. In one embodiment, clips or mechanical fasteners are provided to allow attachment of the thruster to a lid speculum.

Figure 24:
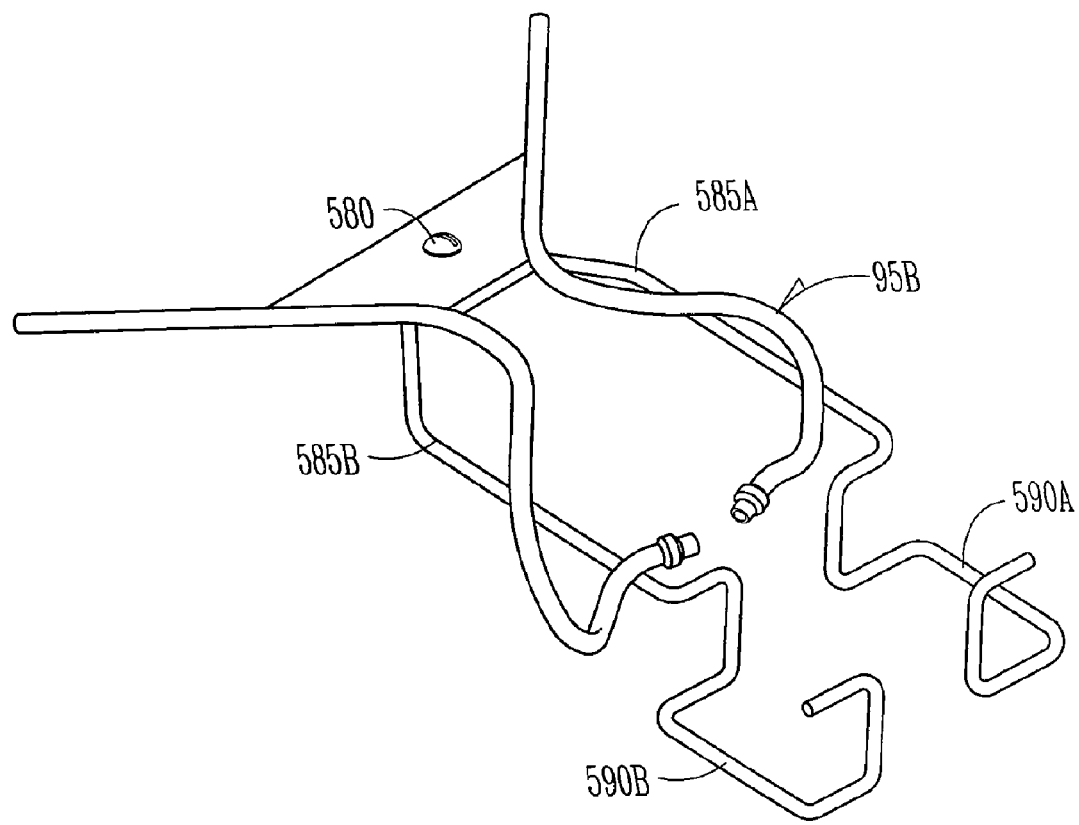
FIG. 24 illustrates an introducer with speculum blades.

FIG. 24 illustrates one embodiment of an introducer integrated with a speculum. In the figure, introducer 95B includes a pair of formed tubular legs held in rigid alignment by a joining strut. The legs of introducer 95B are configured to facilitate introduction of track 110 about the bony orbit of an eye, and in the embodiment shown, the legs do not cross each other. Blades 590A and 590B are coupled to speculum legs 585A and 585B, respectively, and formed to hold the eyelids in a fixed position. Speculum legs 585A and 585B, in one embodiment, are fabricated of spring steel. Blades 590A and 590B are fabricated of wire stock. Joint 580, in one embodiment, includes a threaded fastener that couples speculum legs 585A and 585B to the strut of introducer 95B. In one embodiment, joint 580 includes a flexible coupling that allows legs 585A and 585B to be positioned at an angle relative to introducer 95B. In various embodiments, joint 580 includes a ball and socket joint, a universal joint, a plastic hinge joint or other coupling allowing introducer 95B to be positioned without interfering with the placement of blades 590A and 590B. A spring wire-type speculum is illustrated, however, other types of specula are also contemplated.

In various embodiments, joint 580 includes coupling that allows the specula to be quickly affixed to the introducer without the use of tools. For example, in one embodiment, the joint includes fittings on the specula and the introducer which allows the specula to be clipped into position on the introducer during the course of a surgical procedure. In one embodiment, the joint includes a fastener or clip at an edge (or surface) of the strut and a matching fastener or clip on the specula. In one embodiment, the specula is positioned substantially underneath the introducer. In one embodiment, the introducer is positioned substantially underneath the specula.

Figure 25:
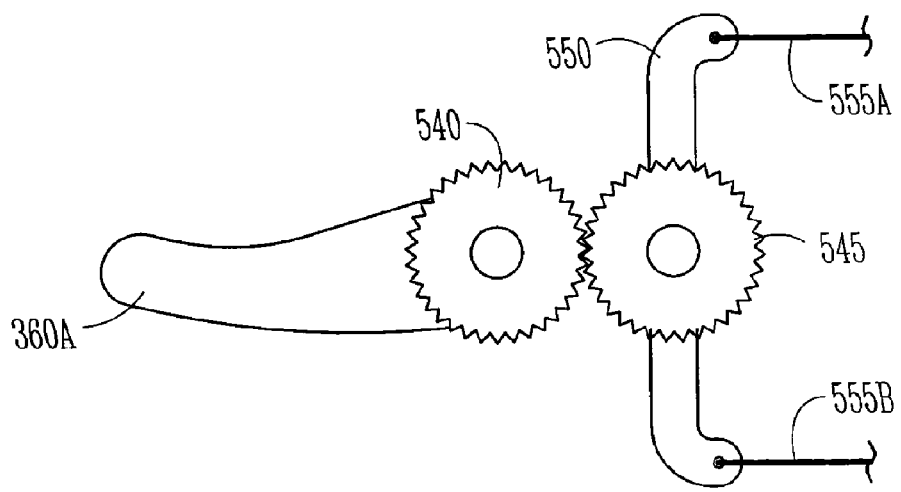
FIG. 25 illustrates a bell crank operated thruster.

In one embodiment, a bell crank assembly is coupled to the thruster. FIG. 25 illustrates thruster 360 adapted to pivot on a shaft and coupled to concentric sprocket 540. Sprocket 545 engages the teeth of sprocket 540 and is rigidly coupled to bell crank 550. Bell crank 550 is coupled to line 555A and line 555B. A suitable force applied to line 555A or line 555B will deploy or retract thruster 360.

In one embodiment, line 555A includes a rigid shaft and line 555B is omitted. A force applied to line 555A will deploy or retract thruster 360.

In one embodiment, the thruster includes a flexible tip or contact surface.

In one embodiment, each thruster, of a plurality of thrusters, is independently retractable or deployable. In one embodiment, each thruster can be positioned independent of the position of other thrusters. In one embodiment, the degree of extension or retraction of each thruster can be independently selected.

In one embodiment, a transcleral light source is positioned around the eye using track 110 and introducer 95A and no thruster or balloon is included in track 110.

In one embodiment, track 110 includes an endless loop and a ring gear or other structure within track 110 is used to position a thruster.

In one embodiment, introducer 95A facilitates insertion of a partial loop of track 110 about the bony orbit.

Figure 26:
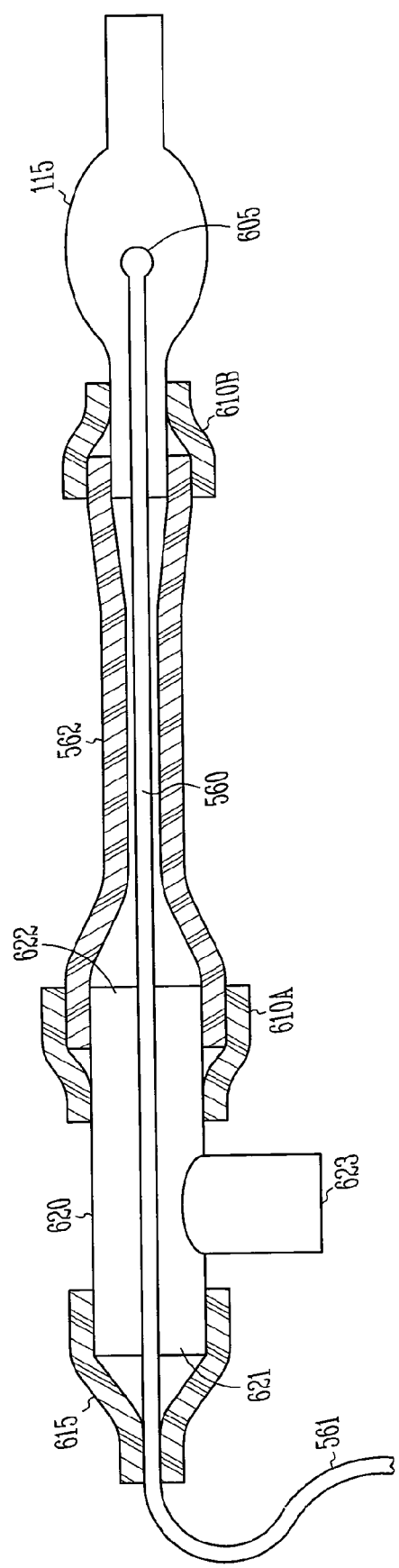
FIG. 26 includes an illuminated portion of one embodiment of the present subject matter.

FIG. 26 illustrates one embodiment of the present subject matter including fiber optic element 560 configured to illuminate balloon 115. End 561 of fiber optic element 560 is coupled to a light source. Coupling 615, in one embodiment, includes a heat shrink tubing that rigidly affixes fiber optic element 560 to port 621 of three-port fitting 620. Port 622 is coupled to Teflon® tube 562 by coupling 610A. Port 623 is coupled to a pressure source for controlling inflation and deflation of balloon 115. Fiber optic element 560 is positioned within tube 562 and terminates at end 605 within balloon 115. Coupling 610B couples tube 562 to a first stem of balloon 115. A second stem of balloon 115 is sealed closed.

Fiber optic element 560, in one embodiment, includes a side emitting element. End 605 is adapted to disperse light from within element 560. In one embodiment, end 560 includes a generally spherical shape formed by heating and molding.

End 605 is held in position within balloon 115 by the structure described herein and, in one embodiment, aids in positioning the balloon at a point for application of a thrusting force.

Balloon 115 is spaced apart from fitting 620 by a sufficient dimension such that balloon 115 can be suitably positioned to apply pressure to the sclera as described herein. In one embodiment, fitting 620 is external to the bony orbit and balloon 115 is within the bony orbit. In one embodiment, fitting 620 is a straight coupling with no "T" connection, or port, as shown at 623, and a source of air pressure is injected into balloon 115 at coupling 615.

Figure 27A:
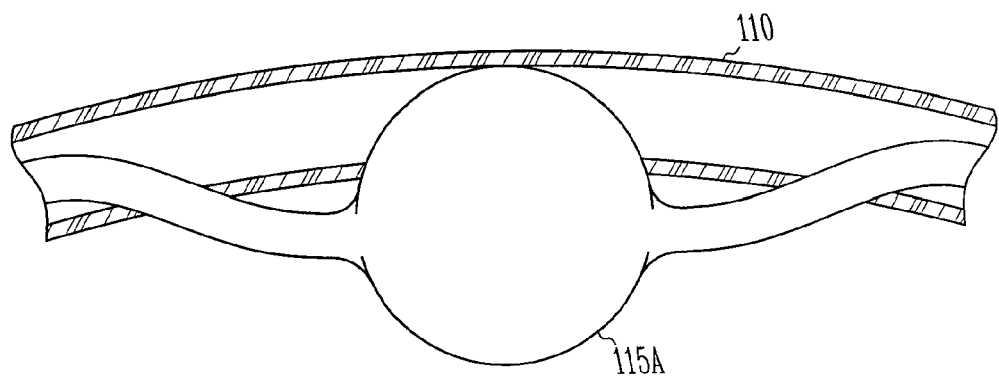
FIG. 27A includes a balloon portion of one embodiment of the present subject matter.
Figure 27B:
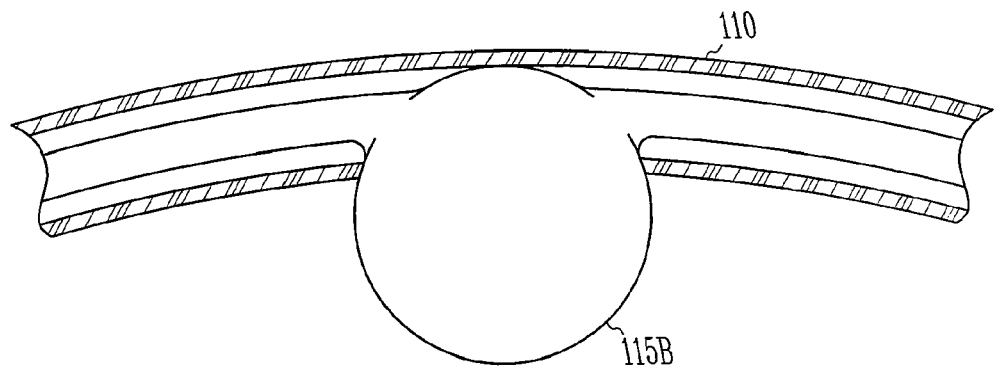
FIG. 27B includes a balloon portion of one embodiment of the present subject matter.

FIG. 27A illustrates a portion of an embodiment having balloon 115A disposed in track 110. As shown in the figure, when balloon 115A is inflated, portions of the balloon stems are drawn out of the slot of track 110. FIG. 27B illustrates an embodiment wherein balloon 115B is adapted such that the stems remain wholly within the lumen of track 110. In FIG. 27B, the stems of balloon 115B are coupled to the spherical portion at a location offset from a centerline of the balloon.

Other methods of retaining balloon stems within the lumen of track 110 are also contemplated. For example, in one embodiment, an adhesive coating is applied to a backside portion of balloon 115 to restrict inflation of that portion, thereby shifting a greater amount of displacement to other portions of the balloon. In one embodiment, the wall thickness of balloon 115 is molded to force inflation to be greater in one dimension as compared to another dimension. In one embodiment, an outer sleeve with a hole is positioned over balloon 115, thereby controlling the direction of inflation.

Figure 28:
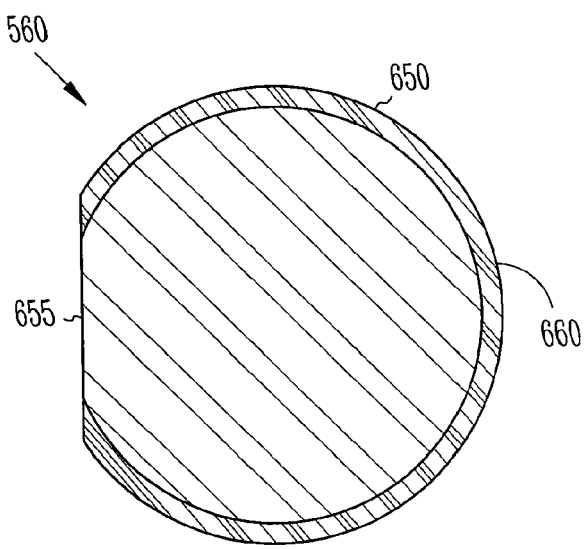
FIG. 28 includes a section view of a fiber optic element portion of one embodiment of the present subject matter.

FIG. 28 includes a section view of fiber optic element 560 according to one embodiment. Exposed region 655 is devoid of cladding 650 and thus, light within element 560 will be projected at a greater intensity from region 655. In one embodiment, at region 660, a light reflective coating is applied to direct illumination into region 655.

Figure 29:
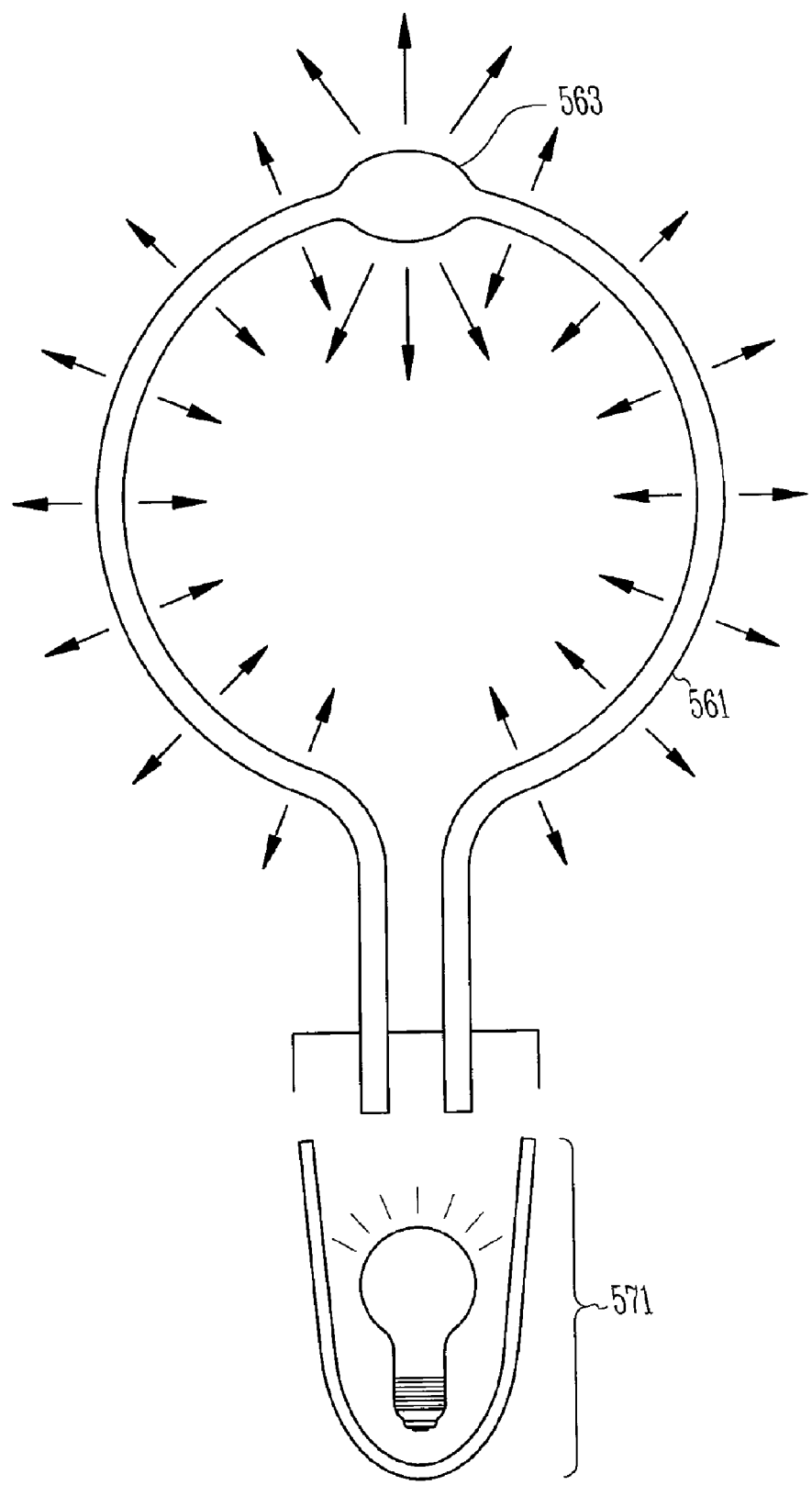
FIG. 29 includes a view of a double ended fiber optic element portion of one embodiment of the present subject matter.

FIG. 29 includes a continuous loop of side emitting fiber optic element 561. Element 561 includes a shaped portion 563 adapted to provide additional illumination, as denoted by the relative sizes of arrows distributed about element 561. Light source 571 illuminates both ends of element 561. In one embodiment, portion 563 is fabricated by heating and exerting a compressive force on each end to form a thickened, or generally spherical region along the length of element 561. Portion 563, in one embodiment is aligned with the center of balloon 115 to aid in placement of balloon 115 within the track.

Figure 30A:
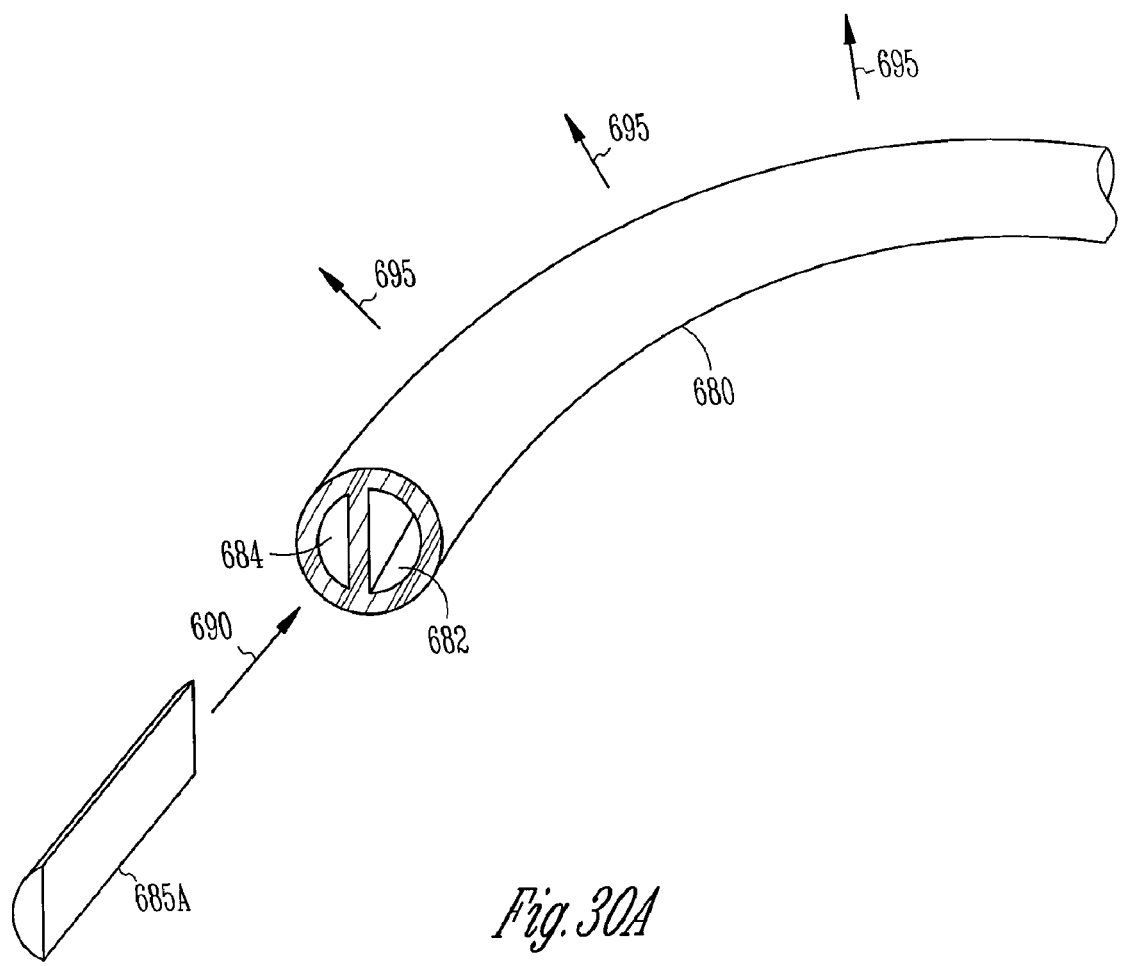
FIG. 30A includes a view of a two-lumen track with a spring element according to one embodiment of the present subject matter.

FIG. 30A includes an embodiment for immobilizing the present subject matter within the bony orbit of an eye. In the figure, tube 680 includes first lumen 684 and second lumen 682. Second lumen 682 is adapted to receive a fiber optic element, a balloon or other thruster device as described herein. First lumen 684 is adapted to receive flat spring 685A. Flat spring 685A, in the figure, has a "D" shape cross section and is adapted to urge tube 680 in a direction towards an increased major diameter, thus applying a greater holding force within the bony orbit. In various embodiments, spring 685A includes a metal leaf spring, a shape memory material, a coil spring, a non-metallic spring or other material or structure.

In one embodiment, the track is fabricated with structure to aid in immobilizing the track within the bony orbit. In one embodiment, the structure includes a series of ribs, knobs or other raised portions to improve the grip with the bony orbit.

Figure 30B:
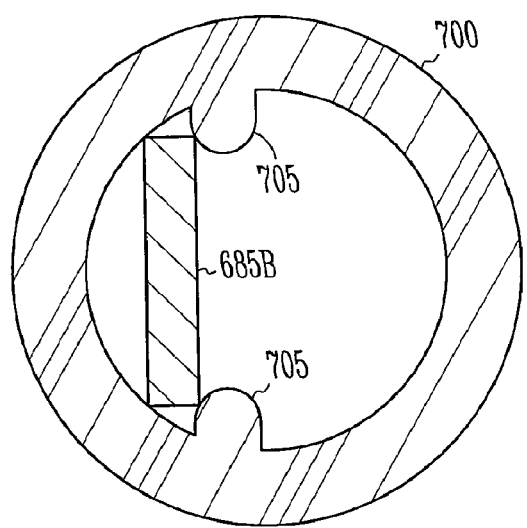
FIG. 30B includes a section view of a track with a spring element according to one embodiment of the present subject matter.

FIG. 30B includes a section view of tube 700 and formed ridges 705. Spring 685B is captivated by the wall of tube 700 and ridges 705. In one embodiment, a spring fits within linear grooves on the inside surface of tube 700.

In one embodiment, undesirable heating from the fiber optic element can be ameliorated by circulating cooling air through the track of the present subject matter. Cooling air can be circulated by a vacuum or pressure system coupled to an end of the track. In one embodiment, a cooling fluid, such as a saline solution or water, is circulated.

In one embodiment, an end emitting fiber optic element is positioned within balloon 115. The end of the element is polished or shaped to aid in readily identifying the position of the balloon during a surgical procedure.

CONCLUSION

The above description is intended to be illustrative, and not restrictive. Many other embodiments will be apparent to those of skill in the art upon reviewing the above description.

What is claimed is:

1. A method comprising:
   positioning a guide member around at least a portion of an eye, the guide member providing access to at least a first region of the eye, the first region disposed radially about the eye;
   positioning a first thruster independent of the positioning of the guide member, the first thruster positioned proximate to the first region; and actuating the first thruster to exert a first force on the eye at the first region, the first force relative to the guide member.

2. The method of claim 1 further comprising:

positioning a second thruster relative to the guide member at a second region disposed radially about the eye; and actuating the second thruster to exert a second force on the eye at the second region, the second force relative to the guide member.

3. The method of claim 2 wherein positioning the second thruster is independent of positioning of the first thruster.

4. The method of claim 2 wherein actuating the second thruster is independent of actuating the first thruster.

5. The method of claim 1 wherein positioning the guide member includes at least one of any combination of encircling at least a portion of the eye and positioning within a bony orbit of the eye.

6. The method of claim 1 wherein positioning the first thruster includes at least one of any combination of exerting a linear force about the eye and receiving a signal from a remote controller.

7. The method of claim 1 wherein actuating the first thruster includes at least one of any combination of receiving a signal from a remote controller, exerting a linear force about the eye, introducing a fluid to an envelope, pumping a fluid into a balloon, articulating a link arm, transforming a shape memory material, exerting a spring force and selecting a radial extension dimension.

* * * * *